(12) United States Patent
Sharma et al.

(10) Patent No.: US 8,639,323 B2
(45) Date of Patent: Jan. 28, 2014

(54) SYSTEM AND APPARATUS TO MONITOR BIOPACEMAKER MATURATION

(75) Inventors: Vinod Sharma, Maple Grove, MN (US); Deborah A. Jaye, Shoreview, MN (US); Daniel Sigg, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 12/917,062

(22) Filed: Nov. 1, 2010

(65) Prior Publication Data
US 2012/0109231 A1    May 3, 2012

(51) Int. Cl.
*A61N 1/08* (2006.01)
(52) U.S. Cl.
USPC .................................. 607/3; 607/28
(58) Field of Classification Search
USPC ............................. 607/3, 27, 28, 19
See application file for complete search history.

(56) References Cited

U.S. PATENT DOCUMENTS

| 5,417,717 | A | 5/1995 | Salo et al. |
|---|---|---|---|
| 5,464,404 | A | 11/1995 | Abela et al. |
| 5,776,168 | A | 7/1998 | Gunderson |
| 6,214,620 | B1 | 4/2001 | Johns et al. |
| 6,330,476 | B1 | 12/2001 | Ben-Haim et al. |
| 6,376,471 | B1 | 4/2002 | Lawrence, III et al. |
| 6,609,023 | B1 * | 8/2003 | Fischell et al. ............ 600/515 |
| 6,718,204 | B2 | 4/2004 | DeGroot et al. |
| 6,818,757 | B2 | 11/2004 | Lee et al. |
| 6,892,094 | B2 | 5/2005 | Ousdigian et al. |
| 6,922,585 | B2 | 7/2005 | Zhou et al. |
| 7,013,178 | B2 | 3/2006 | Reinke et al. |
| 7,034,008 | B2 | 4/2006 | Donahue et al. |
| 7,107,098 | B2 | 9/2006 | Sharma et al. |
| 7,120,484 | B2 | 10/2006 | Lu et al. |
| 7,142,928 | B2 | 11/2006 | Sharma et al. |
| 7,149,577 | B2 | 12/2006 | Sharma et al. |
| 7,177,680 | B2 | 2/2007 | Sharma et al. |
| 7,190,993 | B2 | 3/2007 | Sharma et al. |
| 7,392,082 | B2 | 6/2008 | Sharma |
| 7,415,307 | B2 | 8/2008 | Sharma et al. |
| 7,515,960 | B2 | 4/2009 | Sharma |
| 7,608,458 | B2 | 10/2009 | Soykan et al. |
| 7,622,303 | B2 | 11/2009 | Soykan et al. |

(Continued)

FOREIGN PATENT DOCUMENTS

| WO | WO 98/02150 A1 | 1/1998 |
|---|---|---|
| WO | WO 02/19966 A2 | 3/2002 |

(Continued)

OTHER PUBLICATIONS

Bailey and Posse, "13. Manipulation of Baculovirus vectors," pp. 147-168 in *Methods in Molecular Biology*, vol. 7: *Gene Transfer and Expression Protocols*. Humana Press: Clifton, NJ; 1991.
Benson et al., "GenBank," 1997 *Nucleic Acids Res*. 25:1-6.
Bucchi et al., "Wild-type and mutant HCN channels in a tandem biological-electronic cardiac pacemaker," Sep. 2006 *Circulation* 114:992-999. Available online on Aug. 21, 2006.
Clark et al., "Cell lines for the production of recombinant adeno-associated virus," Oct. 1995 *Human Gene Ther*. 6:1329-1341.
Cribbs et al., "Cloning and characterization of α1H from human heart, a member of the T-type $Ca^{2+}$ channel gene family," Jul. 13, 1998 *Circulation Res*. 83:103-109.

(Continued)

*Primary Examiner* — Christopher D Koharski
*Assistant Examiner* — Michael Carey

(57) ABSTRACT

The present invention includes systems, devices, and methods relating to the monitoring of the functional maturation of biological interventions effecting cardiac pacing; the systems, devices, and methods including an implantable electronic pulse generator delivering artificial cardiac pacing; a means for halting the electronic pulse generator delivering artificial cardiac pacing at predetermined data collection intervals; and a sensor for recording and storing data on one or more intrinsic physiological parameters of cardiac pacing during the predetermined data collection intervals.

39 Claims, 21 Drawing Sheets

(56) References Cited

U.S. PATENT DOCUMENTS

| | | | |
|---|---|---|---|
| 7,778,705 | B2 | 8/2010 | Sigg et al. |
| 2002/0022259 | A1 | 2/2002 | Lee et al. |
| 2002/0095190 | A1* | 7/2002 | Bornzin et al. ............... 607/28 |
| 2002/0155101 | A1 | 10/2002 | Donahue et al. |
| 2004/0181259 | A1 | 9/2004 | DeGroot et al. |
| 2004/0214182 | A1 | 10/2004 | Sharma et al. |
| 2004/0215251 | A1 | 10/2004 | Sharma et al. |
| 2005/0021089 | A1 | 1/2005 | Sharma |
| 2006/0020316 | A1 | 1/2006 | Martinez et al. |
| 2006/0088503 | A1 | 4/2006 | Sharma et al. |
| 2006/0247697 | A1 | 11/2006 | Sharma et al. |
| 2007/0021375 | A1 | 1/2007 | Sharma et al. |
| 2007/0087033 | A1 | 4/2007 | Sigg et al. |
| 2007/0099268 | A1* | 5/2007 | Cohen et al. ............... 435/69.1 |
| 2007/0156189 | A1 | 7/2007 | DeGroot et al. |
| 2008/0103537 | A1 | 5/2008 | Sigg et al. |
| 2008/0200769 | A1 | 8/2008 | Sharma et al. |
| 2008/0281371 | A1* | 11/2008 | KenKnight et al. ............ 607/19 |
| 2009/0099611 | A1* | 4/2009 | Sigg et al. ....................... 607/3 |
| 2009/0157129 | A1 | 6/2009 | Sharma |
| 2010/0047915 | A1 | 2/2010 | Soykan et al. |
| 2010/0076063 | A1 | 3/2010 | Sharma et al. |

FOREIGN PATENT DOCUMENTS

| | | |
|---|---|---|
| WO | WO 02/33111 A2 | 4/2002 |
| WO | WO 02/019966 A3 | 8/2002 |
| WO | WO 02/087419 A2 | 11/2002 |
| WO | WO 02/033111 A3 | 12/2002 |
| WO | WO 02/098286 A2 | 12/2002 |
| WO | WO 02/98286 A3 | 5/2003 |
| WO | WO 02/87419 A3 | 2/2004 |
| WO | WO 2004/093969 A1 | 11/2004 |
| WO | WO 2005/062890 A2 | 7/2005 |
| WO | WO 2005/062958 A2 | 7/2005 |
| WO | WO 2005/062890 A3 | 8/2006 |
| WO | WO 2005/062958 A3 | 5/2007 |
| WO | WO 2007/126887 A2 | 11/2007 |
| WO | WO 2007/126887 A3 | 2/2008 |

OTHER PUBLICATIONS

Felgner, "8. Cationic liposome-mediated transfection with Lipofectin™ reagent," in *Methods in Molecular Biology*, vol. 7: *Gene Transfer and Expression Protocols*. Humana Press: Clifton, NJ; 1991. Cover page and pp. 81-89.

Glenn et al., "Gene therapy to develop a genetically engineered cardiac pacemaker," Nov.-Nov./Dec. 2003 *J. Cardiovascular Nursing* 18:330-336.

Graham et al., "11. Manipulation of adenovirus vectors," pp. 109-128 in *Methods in Molecular Biology*, vol. 7: *Gene Transfer and Expression Protocols*. Humana Press: Clifton, NJ; 1991.

Guzman et al., "Efficient gene transfer into myocardium by direct injection of adenovirus vectors," Dec. 1993 *Circulation Res.* 73(6):1202-1207.

Hammarskjöld, "14. Manipulation of SV40 vectors," pp. 169-180 in *Methods in Molecular Biology*, vol. 7: *Gene Transfer and Expression Protocols*. Humana Press: Clifton, NJ; 1991.

Ishii et al., "Molecular characterization of the hyperpolarization-activated cation channel in rabbit heart sinoatrial node," Apr. 30, 1999 *J. Biol. Chem.* 274:12835-12839.

Josephson, "Electrophysiologic investigation: general concepts," pp. 22-70 in *Clinical Cardiac Electrophysiology: Techniques and Interpretations*. Lea & Febiger: Philadelphia, PA; 1993.

Kagan et al., "The dominant negative LQT2 mutation A516V reduces wild-type HERG expression," Apr. 14, 2000 *J. Biol. Chem.* 275:11241-11248.

Katz, "T-type calcium channels may provide a unique target for cardiovascular therapy," Jun. 1999 *Eur. Heart J. (Supp. H; The heart rate: a simple concept with unrevealed clinical implications)* H:18-23.

Kirschlhof et al., "Evidence for the presence of electrotonic depression of pacemakers in the rabbit atrioventricular node. The effects of uncoupling from the surrounding myocardium," Mar.-Apr. 1988 *Basic Res. Cardiology* 83:190-201.

LaPointe et al., "Left ventricular targeting of reporter gene expression in vivo by human BNP promoter in an adenoviral vector," Oct. 2002 *Am. J. Physiol.* 283:H1439-1445.

Lee et al., "Cloning and expression of a novel member of the low voltage-activated T-type calcium channel family," Mar. 15, 1999 *J. Neurosci.* 19:1912-1921.

Ludwig et al., "Two pacemaker channels from human heart with profoundly different activation kinetics," May 4, 1999 *EMBO J.* 18:2323-2329.

Mackett, "12. Manipulation of Vaccinia virus vectors," pp. 129-146 in *Methods in Molecular Biology*, vol. 7: *Gene Transfer and Expression Protocols*. Humana Press: Clifton, NJ; 1991.

Miake et al., "Biological pacemaker created by gene transfer," Sep. 12, 2002 *Nature* 419:132-133.

Morgenstern and Land, "15. Choice and manipulation of retroviral vectors," pp. 180-206 in *Methods in Molecular Biology*, vol. 7: *Gene Transfer and Expression Protocols*. Humana Press: Clifton, NJ; 1991.

Plotnikov et al., "Biological pacemaker implanted in canine left bundle branch provides ventricular escape rhythms that have physiologically acceptable rates," Feb. 3, 2004 *Circulation* 109:506-512. Available online on Jan. 20, 2004.

Qu et al., "Expression and function of a biological pacemaker in canine heart," Mar. 4, 2003 *Circulation* 107:1106-1109. Available online on Feb. 24, 2003.

Rosen et al., "Recreating the biological pacemaker," Oct. 2004 *Anat. Rec. Part A: Disc. Mol. Cell. Evol. Biol.* 280:1046-1052. Available online on Sep. 15, 2004.

Schram et al., "Differential distribution of cardiac ion channel expression as a basis for regional specialization in electrical function," May 17, 2002 *Circulation Res.* 90:939-950.

Schnepp et al. "29. Highly purified recombinant adeno-associate virus vectors: Preparation and quantitation," pp. 427-443 in *Gene Therapy Protocols 2nd Edition*. Humana Press: Totowa, NJ; 2002.

Shorofsky et al., "Calcium currents and arrhythmias: insights from molecular biology," Feb. 1, 2001 *Am. J. Medicine* 110:127-140.

Ueda et al., "Functional characterization of a trafficking-defective HCN4 mutation, D553N, associated with cardiac arrhythmia," Jun. 25, 2004 *J. Biol. Chem.* 279:27194-27198. Available online on Apr. 30, 2004.

Vasquez et al., "13. Triplex-directed site-specific genome modification," pp. 183-200 in *Methods in Molecular Biology*, vol. 133: *Gene Targeting Protocols*. University of Delaware: Newark, DE; 2000. Published on Sep. 23, 1999.

Institute of Laboratory Animal Resources Commission on Life Sciences National Research Council, *Guide for the Care and Use of Laboratory Animals*. National Academy Press: Washington, D.C.; copyright 1996. [DHEW(DHHS) publication (NIH) No. 85-23.

Jaye et al., "Ventricular Biological Pacemaker Successfully Created in Canine Model by Human HCN4 Gene Transfer," Meeting Abstract 21428; presented at *Scientific Sessions* 2010; Nov. 14-16: Chicago, IL. American Heart Association. Published in Nov. 23, 2010 *Circulation* 122(21—supplement):A21428. Available online [retrieved on Dec. 21, 2010]. Retrieved from the Internet: <http://circ.ahajournals.org/cgi/content/meeting_abstract/122/21_MeetingAbstracts/A21428>; 3 pages.

TACS•XL™ In Situ Apoptosis Detection Kit: R&D Systems, Inc; Minneapolis, MN. Available online [retrieved on Dec. 21, 2010]. Retrieved from the Internet: <http://www.rndsystems.com/pdf/TA100.pdf >; 24 pages.

(PCT/US2011/055866) PCT Notification of Transmittal of the International Search Report and the Written Opinion of the International Searching Authority, Mailed Dec. 27, 2011, 12 pages.

* cited by examiner

Fig. 9

| | Pacing Rate | Channel Selection | Vector | |
|---|---|---|---|---|
| Reference 1 | 30 bpm | Channel 1 | Atip to Vring | Display |
| Reference 2 | 30 bpm | Channel 1 | Atip to Vring | Display |
| Reference 3 | 30 bpm | Channel 1 | Atip to Vring | Display |
| Reference 4 | 30 bpm | Channel 1 | Atip to Vring | Display |

Note: The Duration of Reference and Vectors are programmed via Parameters Tab / Recording Duration Refresh Create Text File        End Session

Fig. 10

| Periodic EGM Collection | Recording Interval | Recording Duration |
|---|---|---|
| ON | 1 hr | 15 sec |

| Overwrite Oldest Data | VT Monitor | |
|---|---|---|
| NO | NO | |

| Control Pacing Rate | Pacing Rate | Stop Pacing before EGM |
|---|---|---|
| YES | 40 bpm | 60 sec |

Nominals        Clear Pending        Refresh

Create Text File        End Session

| Data View | General Info | | | |
|---|---|---|---|---|
| Information | Summary | Parameters | EGM Controls | Reference EGM |

|  | Pacing Rate | Channel Selection | Vector |  |
|---|---|---|---|---|
| Reference 1 | 30 bpm | Channel 2 | Atip to Aring | Display |
| Reference 2 | 30 bpm | Channel 1 | Vtip to Vring | Display |
| Reference 3 | 30 bpm | Channel 1 | Vtip to Vring | Display |
| Reference 4 | 30 bpm | Channel 2 | Atip to Aring | Display |

Note: The Duration of Reference and Vectors are programmed via Parameters Tab / Recording Duration Refresh

SYSTEM AND APPARATUS TO MONITOR BIOPACEMAKER MATURATION

BACKGROUND

Cardiac contraction in a healthy human heart is initiated by spontaneous excitation of the sinoatrial ("SA") node, which is located in the right atrium. The electric impulse generated by the SA node travels to the atrioventricular ("AV") node where it is transmitted to the bundle of His and to the Purkinje network. The fibers in the Purkinje network branch out in many directions to facilitate coordinated contraction of the left and right ventricles, thus providing natural pacing. In some disease states, the heart loses some of its natural capacity to pace properly. Such dysfunction is commonly treated by implanting a pacemaking device that generates an electronic pulse.

While effectively improving the lives of many patients, such implantable pacemakers have certain technical limitations. For example, implantable pacemakers rely on a self-contained power source such as a battery and consequently have a limited lifetime before the power source is in need of replacement. Hence, an otherwise healthy patient may require multiple surgeries to replace the power source or the entire implantable pacemaker. In addition, implantable pacemaker batteries are large and are usually the bulkiest pacemaker component. A pacemaker's size and capability for implantation in different body regions are typically dictated by the battery size. Also, implantable pacemakers have very limited or no capacity for directly responding to the body's endogenous signaling the way the SA node responds to such signaling, i.e. by a modulation of the heart rate relative to the physiological and emotional state (e.g. sleep, rest, stress, exercise).

Recently, biological methods of influencing a patient's cardiac cells have been developed, some of which include administering biopharmaceutical compositions that affect cardiac pacing. Developments in genetic engineering have produced methods for genetically modifying cardiac cells to modify non-pacemaking cardiac cells to acquire pacemaking capabilities or supply stem cells to regenerate the pacing capabilities of cells in the conduction system of the heart. For example, U.S. Pat. No. 6,214,620 describes a method for modulating the excitability of ventricular cells by controlling the regulation of the expression of certain ion channels (for example, $K^+$ channels), and PCT Publication No. WO 02/087419 and WO 05/062890A3 describe methods and systems for modulating electronic behavior of cardiac cells by genetic modification of inwardly rectifying $K^+$ channels ($I_{K1}$) in quiescent ventricular cells.

Other biological approaches for moderating cardiac pacing involve implanting into the SA node, or other suitable heart regions, cells having particular ion channels that are commonly referred to as hyperpolarization-activated and cyclic nucleotide-gated (HCN) channels. Physiologically originating in the SA node, the HCN channels play a prominent role in the control of rhythmic electrical heart, activity. Cyclic nucleotides modulate HCN channel activity, and channel activation occurs upon hyperpolarization rather than depolarization. There are four isoforms of HCN channels (HCN1-4), and each has greater or lesser prevalence in different heart regions. Because the HCN isoforms are directly involved in pacemaker current modulation and activation, implantation of HCN-expressing cells into cardiac tissue that is diseased or experiencing conduction blockage is a viable method for regulating cardiac pacemaker function. See, for example, PCT Publication Nos. WO 02/098286 and WO 05/062958A2 and U.S. Published Application 20090099611.

Biological pacemakers, implemented using gene or cell based therapies, present great potential and promise as therapeutic alternatives to implantable electronic pacemakers for the treatment of cardiac disorders. However, there is a need for effective methods, systems, and apparatus for monitoring the functional maturation over time of the gene therapy or cell therapy approaches involved in establishing a biological pacemaker and for assessing the success or failure of such biological interventions.

SUMMARY OF THE INVENTION

The present invention includes a method of monitoring the functional effect of an intervention effecting cardiac pacing, the method including halting artificial pacing provided by an implantable electronic pulse generator to a heart subject to an intervention effecting cardiac pacing at predetermined data collection intervals and obtaining data on one or more intrinsic physiological parameters of cardiac pacing in the heart subject to an intervention effecting cardiac pacing during the predetermined data collection intervals.

The present invention includes a method of monitoring the functional effect of an intervention effecting cardiac pacing, the method including providing artificial pacing to a heart with an implantable pulse generator; providing one or more interventions that effect cardiac pacing; halting at predetermined data collection intervals the artificial pacing provided by the implantable electronic pulse generator; and obtaining data on one or more intrinsic physiological parameters of cardiac pacing during the predetermined data collection intervals.

In some aspects of the methods of the present invention, obtaining data on one or more intrinsic physiological parameters of cardiac pacing may be initiated after a predefined interval after the halting of the artificial pacing provided by the implantable electronic pulse generator.

In some aspects of the methods of the present invention, the intervention effecting cardiac pacing includes gene therapy, cell therapy, ablation, and/or drug delivery. In some aspects, the drug is a pharmaceutical drug. In some aspects, the drug is a biological agent, such as for example, a polypeptide, including, but not limited to, a receptor polypeptide or an antibody. In some aspects, gene therapy includes providing a hyperpolarization-activated cyclic nucleotide-gated (HCN) channel gene construct. In some aspects, an intervention effecting cardiac pacing includes cell therapy. In some aspects, cell therapy includes stem cell therapy or genetically modified cell therapy.

In some aspects of the methods of the present invention, an implantable electronic pulse generator includes a pacemaker, ICD, CRT, CRT-D, SubQ ICD, intravascular pacemaker/ICD, and/or miniaturized leadless pacemaker.

In some aspects, a method of the present invention includes monitoring a response of the intervention effecting cardiac pacing to cardiac autonomic function.

In some aspects of the methods of the present invention, providing artificial pacing, halting artificial pacing at predetermined data collection intervals, and/or obtaining data on one or more intrinsic physiological parameters of cardiac pacing during the predetermined data collection intervals may be implemented using programmed instructions. In some aspects, programmed instructions may be executed on a processing circuit included within the implantable electronic pulse generator. In some aspects, programmed instructions may be executed on a processing circuit included external to the implantable electronic pulse generator.

In some aspects of the present invention, the methods further include storing the data on one or more intrinsic physiological parameters of cardiac pacing in memory of the implantable electronic pulse generator. Some aspects further include transmission of stored data to an external device. In some aspects, transmission of the stored data includes uplink telemetry.

In some aspects of the present invention, the methods further include presenting data on one or more intrinsic physiological parameters of cardiac pacing to a user.

In some aspects of the methods of the present invention, an intrinsic physiological parameter of cardiac pacing may be indicative of the establishment of an exogenous biopacing intervention.

In some aspects of the methods of the present invention, an intrinsic physiological parameter of cardiac pacing includes an electrogram (EGM), pressure, cardiac contractability.

In some aspects of the methods of the present invention, artificial pacing may be halted for a period of about 30 seconds to about 180 seconds. In some aspects, data on one or more intrinsic physiological parameters of cardiac pacing may be obtained after a predefined interval after halting artificial pacing.

The present invention includes systems for monitoring the functional effect of an intervention effecting cardiac pacing, the system including an implantable electronic pulse generator delivering artificial cardiac pacing; a means for halting the electronic pulse generator delivering artificial cardiac pacing at predetermined data collection intervals; and a sensor for obtaining data on one or more intrinsic physiological parameters of cardiac pacing during the predetermined data collection intervals.

In some aspects of the systems of the present invention, the system further includes a computer readable medium programmed with instructions, the instructions including instructions for halting the electronic pulse generator delivering artificial cardiac pacing at predetermined data collection intervals; and instructions for obtaining data on one or more intrinsic physiological parameters of cardiac pacing during the predetermined data collection intervals.

In some aspects of the systems of the present invention, the system further includes an external device that provides instructions for halting the electronic pulse generator delivering artificial cardiac pacing at predetermined data collection intervals; and instructions for obtaining data on one or more intrinsic physiological parameters of cardiac pacing during the predetermined data collection intervals.

In some aspects of the systems of the present invention, the system further includes an external device that receives data on the one or more intrinsic physiological parameters of cardiac pacing and presents the data to a user.

The present invention includes a system for monitoring the functional effect of an intervention effecting cardiac pacing, the system including an implantable medical device (IMD) including an electronic pulse generator delivering artificial cardiac pacing, a means of halting the electronic pulse generator delivering artificial cardiac pacing at predetermined data collection intervals, and one or more sensors for obtaining data on one or more intrinsic physiological parameters of cardiac pacing during the predetermined data collection intervals; and a computer readable medium programmed with instructions including halting for a period of time artificial pacing provided the IMD, recording the data on one or more intrinsic physiological parameters of cardiac pacing, and resuming artificial pacing provided by the IMD. In some aspects, the system further includes an external device that provides instruction to the IMD for turning on or off the electronic pulse generator delivering artificial cardiac pacing halting and for obtaining data. In some aspects, the system further includes an external device that receives data on the one or more intrinsic physiological parameters of cardiac pacing and presents the data to a user.

In some aspects of the systems of the present invention, obtaining data on one or more intrinsic physiological parameters of cardiac pacing may be initiated after a predefined interval after the halting of the artificial pacing provided by the implantable electronic pulse generator.

In some aspects of the systems of the present invention, the intervention effecting cardiac pacing includes gene therapy, cell therapy, ablation, and/or drug delivery. In some aspects, the drug is a pharmaceutical drug. In some aspects, the drug is a biological agent, such as for example, a polypeptide, including, but not limited to, a receptor polypeptide or an antibody. In some aspects, gene therapy includes providing a hyperpolarization-activated cyclic nucleotide-gated (HCN) channel gene construct. In some aspects, the intervention effecting cardiac pacing includes cell therapy. In some aspects, cell therapy includes stem cell therapy or genetically modified cell therapy.

In some aspects of the systems of the present invention, the implantable electronic pulse generator includes a pacemaker, ICD, CRT, CRT-D, SubQ ICD, intravascular pacemaker/ICD, and/or miniaturized leadless pacemaker.

In some aspects, a system of the present invention includes monitoring a response of the intervention effecting cardiac pacing to cardiac autonomic function.

In some aspects of the systems of the present invention, the system further includes programmed instructions for providing artificial pacing; halting artificial pacing at predetermined data collection intervals; and/or obtaining data on one or more intrinsic physiological parameters of cardiac pacing during the predetermined data collection intervals. In some aspects, the programmed instructions may be executed on a processing circuit included within the implantable electronic pulse generator. In some aspects, the programmed instructions may be executed on a processing circuit included external to the implantable electronic pulse generator.

In some aspects of the systems of the present invention, the system further includes a means for storing the data on one or more intrinsic physiological parameters of cardiac pacing in memory of the implantable electronic pulse generator. In some aspects, the system further includes a means for the transmission of stored data to an external device. In some aspects, transmission of the stored data includes uplink telemetry.

In some aspects of the systems of the present invention, the system further includes a means for presenting data on one or more intrinsic physiological parameters of cardiac pacing to a user.

In some aspects of the systems of the present invention, an intrinsic physiological parameter of cardiac pacing may be indicative of the establishment of an exogenous biopacing intervention.

In some aspects of the systems of the present invention, an intrinsic physiological parameter of cardiac pacing includes an electrogram (EGM), pressure, cardiac contractability.

In some aspects of the systems of the present invention, artificial pacing may be halted for a period of about 30 seconds to about 180 seconds. In some aspects, data on one or more intrinsic physiological parameters of cardiac pacing may be obtained after a predefined interval after halting artificial pacing.

The present invention includes a computer program product in a computer readable recordable-type medium, the medium including instructions for accomplishing any of the methods or systems of the present invention.

The present invention includes a computer program product in computer readable recordable type medium, the computer program product including instructions for an electronic pulse generator to deliver artificial cardiac pacing; instructions for halting the electronic pulse generator delivering artificial cardiac pacing at predetermined data collection intervals; and instructions for obtaining data on one or more intrinsic physiological parameters of cardiac pacing during the predetermined data collection intervals.

In some aspects of the present invention, a computer program product in a computer readable recordable-type medium further includes instructions for communicating with an external device that receives data on the one or more intrinsic physiological parameters of cardiac pacing and presents the data to a user.

In some aspects of a computer program product of the present invention, obtaining data on one or more intrinsic physiological parameters of cardiac pacing may be initiated after a predefined interval after the halting of the artificial pacing provided by the implantable electronic pulse generator.

In some aspects of a computer program product of the present invention, the intervention effecting cardiac pacing includes gene therapy, cell therapy, ablation, and/or drug delivery. In some aspects, the drug is a pharmaceutical drug. In some aspects, the drug is a biological agent, such as for example, a polypeptide, including, but not limited to, a receptor polypeptide or an antibody. In some aspects, gene therapy includes providing a hyperpolarization-activated cyclic nucleotide-gated (HCN) channel gene construct. In some aspects, the intervention effecting cardiac pacing includes cell therapy. In some aspects, cell therapy includes stem cell therapy or genetically modified cell therapy.

In some aspects of a computer program product of the present invention, the implantable electronic pulse generator includes a pacemaker, ICD, CRT, CRT-D, SubQ ICD, intravascular pacemaker/ICD, and/or miniaturized leadless pacemaker.

In some aspects, a computer program product of the present invention includes monitoring a response of the intervention effecting cardiac pacing to cardiac autonomic function.

In some aspects of a computer program product of the present invention, instructions for providing artificial pacing; halting artificial pacing at predetermined data collection intervals; and/or obtaining data on one or more intrinsic physiological parameters of cardiac pacing during the predetermined data collection intervals may be implemented using programmed instructions. In some aspects, programmed instructions may be executed on a processing circuit included within the implantable electronic pulse generator. In some aspects, programmed instructions may be executed on a processing circuit included external to the implantable electronic pulse generator.

In some aspects, a computer program product of the present invention further includes instructions for storing the data on one or more intrinsic physiological parameters of cardiac pacing in memory of the implantable electronic pulse generator. In some aspects, a computer program product further includes instructions for transmission of stored data to an external device. In some aspects, transmission of the stored data includes uplink telemetry.

In some aspects, a computer program product of the present invention further includes instructions for presenting data on one or more intrinsic physiological parameters of cardiac pacing to a user.

In some aspects of a computer program product of the present invention, an intrinsic physiological parameter of cardiac pacing may be indicative of the establishment of an exogenous biopacing intervention.

In some aspects of a computer program product of the present invention, an intrinsic physiological parameter of cardiac pacing includes an electrogram (EGM), pressure, cardiac contractability.

In some aspects of a computer program product of the present invention, artificial pacing may be halted for a period of about 30 seconds to about 180 seconds. In some aspects, data on one or more intrinsic physiological parameters of cardiac pacing may be obtained after a predefined interval after halting artificial pacing.

The term "and/or" means one or all of the listed elements or a combination of any two or more of the listed elements.

Unless otherwise specified, "a," "an," "the," and "at least one" are used interchangeably and mean one or more than one.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. Screen shot of the Session Summary Indicators.

FIG. 9. Screen shot of the Reference EGM tab of the BioEGM Data Translation Tool showing pacing rate, channel selection, and vector.

FIG. 10. Screen shot of Parameters tab from BioEGM which includes settings for periodic data collection and back-up pacing.

FIG. 11. Electrograms recorded from the RAtip-RVring vector.

FIG. 15. Screen shots of EGM Controls and Parameters tabs showing programmed options for data collection with the ventricular device.

FIG. 16. Screen shot of the Reference EGM tab of the BioEGM Data Translation Tool showing programmed options for collection of reference EGMs with the ventricular device. The Translation Tool allows the user to display the reference electrogram, while the Acquisition Tool allows the additional functionality of recording reference EGMs.

FIG. 18. Channel 1 recordings from the RV lead showing reference electrograms on Day 0 and periodic electrograms on Day 2 at 10:23. Dotted line represents the transition from ventricular escape rhythm to biological pacing from the LV.

FIG. 19. Channel 2 recordings from the LV lead showing reference electrograms on Day 0 and periodic electrograms from Day 2 at 10:23. Dotted line represents the transition from ventricular escape rhythm to biological pacing from the LV.

FIG. 21. Periodic atrial electrograms show a representative isolated LA beat on Day 1.

DETAILED DESCRIPTION OF ILLUSTRATIVE EMBODIMENTS OF THE PRESENT INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Biological interventions for the treatment of cardiac disorders present great potential and promise. The present invention includes systems, devices, methods, and apparatus relating to the monitoring of the functional maturation of biological interventions influencing cardiac pacing. The present invention may be used with any of a wide variety of interventions that influence cardiac pacing, such as, for example, ablation, and/or drug delivery. In some aspects, the drug is a pharmaceutical drug. In some aspects, the drug is a biological agent, such as for example, a polypeptide, including, but not limited to, a receptor polypeptide or an antibody. It is particularly useful in monitoring the maturation of biological interventions affecting cardiac pacing, such as, for example, gene therapy or cell therapy. Such biological interventions may also be referred to herein as a "biological pacemaker," "biologic pacemaker," "biopacemaker," "biopacer," or "biopacing." The ability to monitor the functional maturation and effect of a biological pacemaker after its instillation into the heart will assist the physician in assessing the success or failure of the intervention and resolve potential complications. Depending on the type of biological pacemaker administered and the heart condition being treated, it may take days or weeks before a biological pacemaker expresses pacing functions. The present invention allows for monitoring the maturation of a biological pacemaker after its instillation and until a functional biopacemaker is obtained.

Figure 1:
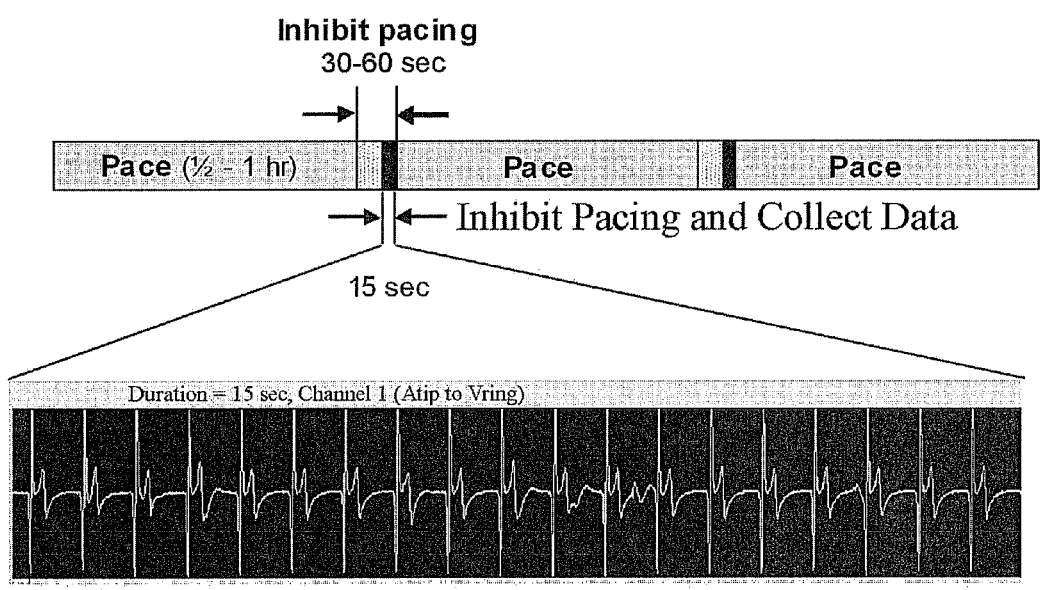
FIG. 1 is an overview of the chronology of one embodiment of the BioEGM of the present invention. Artificial pacing provided by an implantable electronic pulse generator is halted at a predetermined interval (one minute for the present embodiment) during which cardiac electrogram (EGM) data is collected for a predetermined data collection interval (fifteen seconds for the present embodiment).

The present invention allows for monitoring the functional effect of an intervention effecting cardiac pacing by halting, at predetermined intervals, the artificial cardiac pacing being provided by an implantable electronic pulse generator and obtaining data on one or more intrinsic physiological parameters of intrinsic cardiac pacing during these data collection intervals. This is shown in FIG. 1. The present invention may also be referred to herein as a "Bio-pacemaker EGM system," "BioEGM," "BioEGM tool," or "Bio-pacemaker EGM download system."

With the present invention, artificial electronic pacing may be provided to the heart with any of a variety of medical devices that sense data, provide diagnostic information, and/ or deliver therapy. When such a device is implantable (in whole or in part), it is referred to as an implantable medical device (IMD). An IMD may be, for example, an implantable pulse generator (IPG) that delivers electronic pacing therapy. Any of a wide variety of implantable electronic pulse generators may be used, including, but not limited to, pacemaker, implantable cardioverter defibrillator (ICD), cardiac resynchronization therapy (CRT), cardiac resynchronization therapy defibrillation device (CRT-D), subcutaneous ICD (SubQ ICD), intravascular pacemaker/ICD, and/or miniaturized leadless pacemaker. A pacemaker may include, but is not limited to, EnRhythm® pacemaker, Adapta® pacemaker, Versa™ pacemaker, Sensia™ pacemaker, Thera® pacemaker, Prodigy® pacemaker, Priva® pacemaker, and Minuet® pacemaker, all available from Medtronic Inc., Minneapolis, Minn.

An implantable electronic pulse generator (IPG) delivers cardiac pacing therapy to the heart in the faun of one or more electrical stimulation signals via one or more electrodes of an implantable lead connected to the IPG. The IPG may be configured to generate and deliver pacing therapy according to a variety of electrical stimulation parameters, which may include amplitude, pulse width, pulse rate, electrode combination, electrode polarity, and the like. The specific values for these parameters influence the effectiveness of the pacing therapy in achieving adequate capture of the heart. Capture generally refers to the pacing therapy causing sufficient depolarization of the myocardium that a propagating wave of excitation and contraction results, which may be considered a heartbeat. An implantable electronic pulse generator may also provide cardiac monitoring capabilities, alternate cardiac therapies, non-cardiac monitoring and/or non-cardiac therapies.

With the present invention, artificial electronic pacemaking provided by an IPG is halted at various intervals, so that data on intrinsic physiological parameters of cardiac pacing may be collected and recorded. Intrinsic physiological parameters of cardiac pacing include, but are not limited to, cardiac electrogram (EGM), cardiac contractability, intracardiac blood pressure, intravascular blood pressure, blood flow, blood oxygen, and electrocardiogram (ECG). The BioEGM tool of the present invention may gather specialized data on physiological parameters of cardiac pacing. For example, data on the morphology of ectopic beats may be gathered to assist in a determination of whether such an ectopic beat is coming from the injection site at which a biological pacemaker therapy was delivered. The BioEGM tool may record VT episodes in case biologic intervention is proarrhythmic.

The Bio-pacemaker EGM may perform any of a variety of calculations using data collected on physiological parameters of cardiac function, including, but not limited to, heart rate variability analysis, night and day heart rate calculations, and other assessments of the responsiveness of the biological pacemaker to cardiac autonomic function.

The Bio-pacemaker EGM allows for device-based EGM data collection on a periodic basis. Thus, the Bio-pacemaker EGM download program will enable the device to perform periodic storage of intrinsic physiological parameters of cardiac function, including, but not limited to, normal sinus/ intrinsic rhythm (NSR). EGM. The program will help in the bio-pacemaker experiments by helping to elucidate time course for expression of exogenously delivered genes. Thus, the Bio-pacemaker EGM study is particularly useful for investigational use in animal studies.

In addition to periodically collecting data at predetermined intervals, the Bio-pacemaker EGM may include a means for data collection that is triggered by an event. Inhibition of pacing and data collection may be triggered, for example, when a programmed heart rate, average heart rate, or heart rate condition is met, a specified time interval has elapsed, or when an observer or the patient initiates a recording interval. Such data collection may be periodic or may be continuous long duration capture.

In some aspects, the Bio-pacemaker EGM may include a means for changing from the periodic capture of data to the continuous long duration capture of data. In some aspects, such a change may be triggered, for example, when a programmed heart rate, average heart rate, or heart rate condition is met, a specified time interval has elapsed, or at the initiation of an observer or the patient.

Pacing may be halted at predetermined intervals during pacing. The time between such intervals may be, for example, about fifteen minutes, about thirty minutes, about an hour, about one and a half hours, about two hours, about three hours, about four hours, about six hours, about eight hours, about twelve hours, about twenty-four hours, or any interval of the above referenced times.

Artificial electronic pacemaking is halted for an interval of time sufficient to allow for the collection and recordation of data on intrinsic physiological parameters of cardiac pacing. Such an interval of time may be, for example, about 1 second, about 2 seconds, about 5 seconds, about 10 seconds, about 20 seconds, about 30 seconds, about 40 seconds, about 45 seconds, about 50 seconds, about 60 seconds, about 90 seconds, about 100 seconds, about 120 seconds, about 150 seconds, about 180 seconds, about 200 seconds, about 240 seconds, about 300 seconds, about 360 seconds, or any interval of the above referenced times.

Data on one or more intrinsic physiological parameters of cardiac pacing may be collected and recorded for a length of time, also referred to herein as a recording interval. For example, data may be collected and recorded for about 1 second, about 2 seconds, about 5 seconds, about 10 seconds, about 15 seconds, about 20 seconds, about 30 seconds, about 40 seconds, about 45 seconds, about 50 seconds, about 60 seconds, about 75 seconds, about 90 seconds, about 120 seconds, about 150 seconds, about 180 seconds, or any interval of the times referenced above. The IPG may include a sensing module that collects and records the data obtained on parameters of cardiac pacing.

Data on one or more intrinsic physiological parameters of cardiac pacing may be collected and recorded during the entire time period in which artificial pacing is halted, or for any a portion of the time that artificial pacing is halted. For example, in some embodiments, obtaining data on intrinsic physiological parameters of cardiac pacing is initiated after a defined interval of time after the halting of the artificial pacing. Such a pause before the collection and recording of intrinsic data on cardiac pacing may be, for example, about 1 second, about 2 seconds, about 5 seconds, about 10 seconds, about 15 seconds, about 20 seconds, about 30 seconds, about 40 seconds, about 45 seconds, about 50 seconds, about 60 seconds, about 75 seconds, about 90 seconds, about 100 seconds, about 120 seconds, about 150 seconds, about 180 seconds, about 200 seconds, about 240 seconds, about 300 seconds, about 360 seconds, or any interval of the above referenced times. In some embodiments, the BioEGM provides instructions for an interval of halted pacing followed immediately by instructions for an interval of halted pacing and data collection and recording.

In preferred embodiments providing artificial pacing, halting artificial pacing at data collection intervals; and/or obtaining data on one or more intrinsic physiological parameters of cardiac pacing is implemented using programmed instructions. Such programmed instructions may be executed on a processing circuit included within the IPG or on a processing circuit external to the IPG. The IPG may interact with a programmer to allow a user to view and manage data and information stored on the IPG and/or to change the operation parameters of the IPG. Data on cardiac physiological parameters may be stored in memory of the IPG. Stored data may be transmitted to an external device, including, for example, by uplink telemetry.

The present invention and/or one or more portions thereof may be implemented in hardware or software, or a combination of both. For example, the functions described herein may be designed in conformance with the principles set forth herein and implemented as one or more integrated circuits using a suitable processing technology, e.g., CMOS. As another example, the present invention may be implemented using one or more computer programs executing on programmable computers, such as computers that include, for example, processing capabilities, data storage (e.g., volatile and nonvolatile memory and/or storage elements), input devices, and output devices. Program code and/or logic described herein are applied to input data to perform functionality described herein and generate desired output information. The output information may be applied as an input to one or more other devices and/or processes, in a known fashion. Any program used to implement the present invention may be provided in a high level procedural and/or object orientated programming language to communicate with a computer system. Further, programs may be implemented in assembly or machine language. In any case, the language may be a compiled or interpreted language. Any such computer programs may preferably be stored on a storage media or device (e.g., ROM or magnetic disk) readable by a general or special purpose program, computer, or a processor apparatus for configuring and operating the computer when the storage media or device is read by the computer to perform the procedures described herein. The system may also be considered to be implemented as a computer readable storage medium, configured with a computer program, where the storage medium so configured causes the computer to operate in a specific and predefined manner to perform functions described herein. Such a computer readable medium may include only forms of non-transitory tangible media, excluding transitory propagating signals per se.

The present invention and/or one or more portions thereof include circuitry that may include a computer system operable to execute software to provide for periodic halting artificial electronic pacing.

The present invention and/or one or more portions thereof include circuitry that may include a computer system operable to execute software to provide for the determination of one or more physiological parameters of cardiac function.

Although the circuitry may be implemented using software executable using a computer apparatus, other specialized hardware may also provide the functionality required to provide a user with information as to the physiological state of the individual. As such, the term circuitry as used herein includes specialized hardware in addition to or as an alternative to circuitry such as processors capable of executing various software processes. The computer system may be, for example, any fixed or mobile computer system, e.g., a personal computer or a minicomputer. The exact configuration of the computer system is not limiting and almost any device capable of providing suitable computing capabilities may be used according to the present invention. Further, various peripheral devices, such as a computer display, a mouse, a keyboard, memory, a printer, etc., are contemplated to be used in combination with a processing apparatus in the computer system. In view of the above, it will be readily apparent that the functionality as described herein may be implemented in any manner as would be known to one skilled in the art.

The systems, devices, methods and apparatus of the present invention are particularly useful with any of a wide variety of biologic therapies for cardiac disorders, including biopacemakers using gene or cell based therapies for modulating cardiac contraction to desired levels. Biopacing interventions may be administered to any region of the heart, including, but not limited to the right ventricle, right atrium, and/or SA node. Cell based therapies include, but are not limited to, therapies based on the administration of stem cells or genetically engineered cells. Gene therapy includes the delivery of a modified or unmodified polynucleotide.

A polynucleotide may also be referred to herein as "polynucleotide sequence," "nucleic acid," "nucleic acid sequence," "nucleotide sequence," and similar terms. As used herein, the terms "encodes," "encoding," "coding sequence," and similar terms refer to a nucleic acid sequence that is transcribed (in the case of DNA) and translated (in the case of mRNA) into a polypeptide in vitro or in vivo when placed under control of appropriate regulatory sequences. Polynucleotides can be made by traditional PCR-based amplification and known cloning techniques. Alternatively, a polynucleotide can be made by automated procedures that are well known in the art. A polynucleotide may include a start codon to initiate transcription and a stop codon to terminate translation. Suitable polynucleotides for use with the invention may be obtained from a variety of sources including, without limitation, GenBank (National Center for Biotechnology Information (NCBI)), EMBL data library, SWISS-PROT (University of Geneva, Switzerland), the PIR-International database; and the American Type Culture Collection (ATCC)(10801 University Boulevard, Manassas, Va. 20110-2209).

Any suitable vector or delivery vehicle may be utilized to transfer the desired nucleotide sequence to the targeted cardiac cells. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to those of skill in the art.

A vector may be an expression vector. In various embodiments, the expression vectors are packaged into viruses and are delivered in proximity to targeted cells, tissue or organs. Suitable viral vectors include, but are not limited to, retroviral vectors, lentiviral vectors, adenoviral vectors, adeno-associated viral vectors, vaccinia viral vectors, and Semliki Forest viral vectors. For example, an expression vector may be packaged into adenoviruses, such as helper-dependent adeno viral vector (HDAd) or adeno-associated virus pseudo-type 9 (AAV2/9). HDAd virus packaging typically elicits less of an immunogenic response in vivo compared to some other adenoviruses and thus allows for longer term expression. AAV2/9 packaging can result in cardiac tropism as well as a prolonged expression time frame. Other viruses of clinical relevance include lentiviruses. Replication deficient lentiviruses are RNA viruses, which can integrate into the genome and lead to long-term functional expression. Viral vectors systems in addition to lentiviral vectors, AAV vectors, and HD AdV may also be used for the delivery of a polynucleotide encoding an ion channel. Alternatively, non-viral delivery systems may be employed. For example, liposomes, DNA complexes, plasmid, liposome complexes, naked DNA, DNA-coated particles, or polymer based systems may be used to deliver the desired sequence to the cells.

A genetic construct may be introduced to the myocardium using any suitable technique. The genetic material may be delivered into the cells by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection (commonly known as lipofection). Transduction refers to the process of transferring nucleic acid into a cell using a DNA or RNA virus. Suitable viral vectors for use as transducing agents include, but are not limited to, retroviral vectors, adeno-associated viral vectors, lentiviral vectors, herpes simplex viral vectors, vaccinia viruses, and Semliki Forest virus vectors.

A polynucleotide may encode, for example, an ion channel, including, but not limited to, a gap junction channel, calcium channel, a sodium channel, a chloride channel, a hyperpolarized activated cyclic nucleotide (HCN) channel, SERCA2a, a non-specific leak channel, a voltage-gated ion channels, or a potassium channel. A potassium ion channel may be one of a large family of mammalian potassium channels, such as for example, Kv1 (shaker), Kv2, Kv3 (Shaw), Kv4 (Shal), Kv5, Kv6, Kv7, Kv8, or Kv9. In one embodiment, the potassium ion channel is Kv1.3. In some aspects, a polynucleotide may encode a modified ion channel. Such modifications include, but are not limited to, modifications that alter, add, or delete one or more amino acids or the ion channel polypeptide, modifications that encode a truncated ion channel polypeptide, and/or modifications that encode a fusion product of an ion channel polypeptide, or portion thereof, and another polypeptide sequence.

Hyperpolarization-activated cyclic nucleotide-gated channels (HCN) serve as ion channels across the plasma membrane of heart and brain cells and are sometimes referred to as "pacemaker channels" because they help to generate rhythmic activity within groups of heart and brain cells. HCN channels are encoded by four genes (HCN1-4). A polynucleotide may encode, for example, HCN1, HCN2, HCN3, or HCN4. See, for example, WO 2005/062958. In some aspects, a polynucleotide may encode a modified HCN ion channel. Such modifications include, but are not limited to, modifications that alter, add, or delete one or more amino acids or the ion channel polypeptide, modifications that encode a truncated ion channel polypeptide, and/or modifications that encode a fusion product of an ion channel polypeptide, or portion thereof, and another polypeptide sequence. See, for example, U.S. Published Application 20090099611.

The systems, devices, methods, and apparatus of the present invention may be applied to any of a variety of organs, including, but not limited to, the heart, the brain, the spine, nerves, lung, bladder, and blood vessels, including veins and arteries. In a preferred embodiment, the present invention is applied to the heart.

Therapeutically effective concentrations and amounts may be determined for each application herein empirically by testing the compounds in known in vitro and in vivo systems, such as those described herein. Dosages for humans or other animals may then be extrapolated therefrom. With the methods of the present invention, the efficacy of the administration of one or more interventions may be assessed by any of a variety of parameters well known in the art.

As used herein, the term "subject" includes, but is not limited to, humans and non-human vertebrates. In preferred embodiments, a subject is a mammal, particularly a human. A subject may be an individual. A subject may be a patient. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

The methods of the present invention include in vitro, ex vivo, and in vivo methods. As used herein "in vitro" is in cell culture and "in vivo" is within the body of a subject.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

The present invention is illustrated by the following examples. It is to be understood that the particular examples, materials, amounts, and procedures are to be interpreted broadly in accordance with the scope and spirit of the invention as set forth herein.

EXAMPLES

Example 1

Bio-Pacer EGM User Interface Application

A Bio-pacemaker EGM system was constructed with the following components; an EnRhythm® pacemaker, Bio-pacemaker EGM RAMware, and a 2090 Programming system. Functional responsibilities of the EnRhythm device relevant to the application of Bio-pacemaker EGM include pacing (providing all pacing output and timing functions for bradycardia pacing), detection (providing detection of sustained tachyarrhythmias, SVT discrimination, and the basic RR Median value), diagnostics (providing detailed data on sustained episodes), and RAMware (providing the existing RAMware hooks used to manipulate pacing functionality and add diagnostics applicable to Biopacemaker EGM). Functional responsibilities of RAMware relevant to the application of Bio-pacemaker EGM include EGM diagnostics, such as the capabilities to capture additional sinus/intrinsic rhythm EGM based on user programmer parameters and to control pacing rate. Functional responsibilities of the 2090 Programming System relevant to the application of Bio-pacemaker EGM include the Bio-pacemaker EGM User Interface and the Standard Vision User Interface. The Bio-pacemaker EGM User Interface provides parameter programming for Bio-pacemaker EGM parameters, provides for injection of RAMware and removal of RAMware, provides Save to Disk capability that captures Bio-pacemaker EGM general information and detailed diagnostic data, provides telemetry communication with the device, and operates only with the EnRhythm device. The Standard Vision User Interface provides parameter programming (with interlock enforcement) for standard EnRhythm parameters, provides display of standard EnRhythm diagnostics, and provides telemetry communication with the device.

The designated programming component is either a product released Medtronic Model 2090 programmer running the target device's application software or the Bio-pacemaker EGM UI application that interfaces with the implanted device via an RF telemetry programming head. The standard programmer device application software provides control and display of the device's standard parameter and data collection settings. The supported programming device is a Medtronic Model 2090 Programmer with a Vision Software Release 1.35 or later. The Bio-pacemaker EGM User Interface supports this. The application allows users to program and inject RAMware only with supported devices.

The Bio-pacemaker EGM allows for device-based EGM data collection on a periodic basis. Mechanism for heart rate triggered EGM collection could also be implemented. In the latter scheme EGM storage of requisite duration is triggered when heart rate or average heart rate condition programmed by the user is met. In the non-triggered implementation, the Biopacemaker EGM download program enables the device to perform periodic storage of normal sinus/intrinsic rhythm (NSR) EGM. The program—helps in the bio-pacemaker experiments by helping to elucidate time course for expression of exogenously delivered genes. Thus, the Bio-pacemaker EGM study may be particularly useful for investigational use in animal studies. The Bio-pacemaker EGM could also be used as an implantable Holter monitor in which a single continuous recording is captured, rather than a periodic capture. Such a continuous capture could be, for example, be time triggered or event triggered (such as, for example, by the elevation in heart rate to a programmed level).

The Bio-pacemaker EGM User Interface runs on the programmer and provides the user control over aspects of the system. It provides for Bio-pacemaker EGM specific parameter programming and the installation (injection) and removal of the RAMware. It is also responsible for relaying the status of the Bio-pacemaker EGM RAMware (e.g. active or disabled). Finally, the saving and presentation of diagnostic data specific to Bio-pacemaker EGM is handled by the Bio-pacemaker EGM User Interface. Because the diagnostics data is programming dependent, a save to disk may be required per session before programming is allowed. When new parameter values are programmed the RAMware is first deactivated and the diagnostic data cleared to allow the coordination of parameter and diagnostic data information.

Figure 2A:
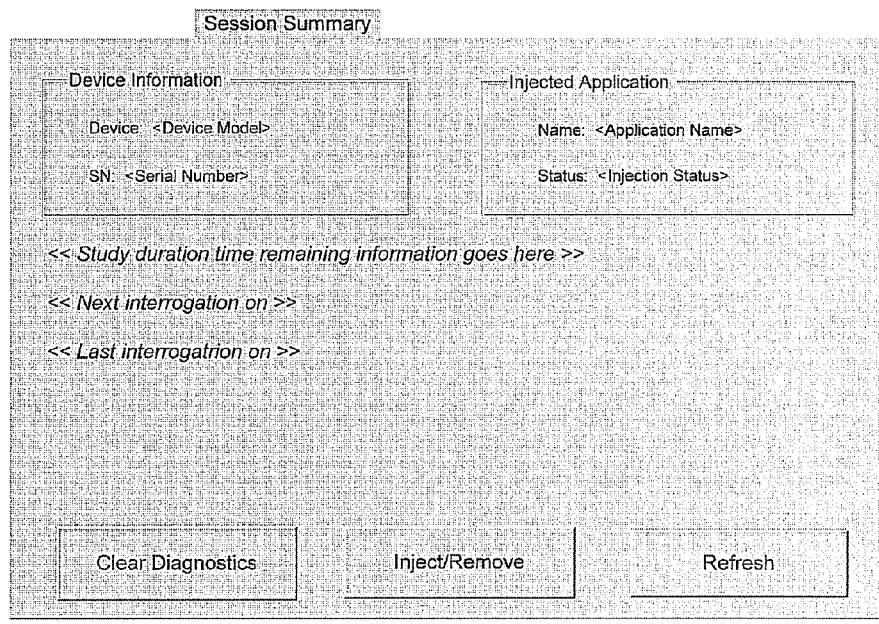
FIG. 2A is a general overview of User Interface Indicators.
Figure 2B:
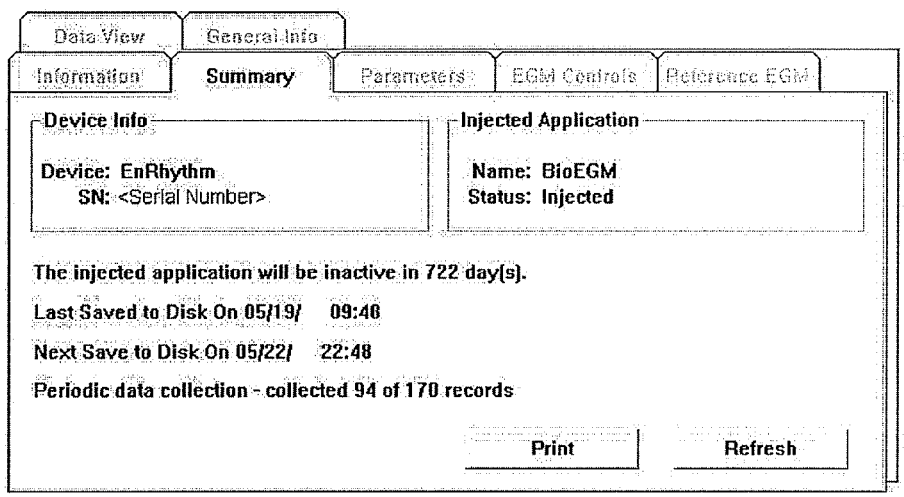
FIG. 2B and FIG. 2C are more detailed screen shots.
Figure 2C:
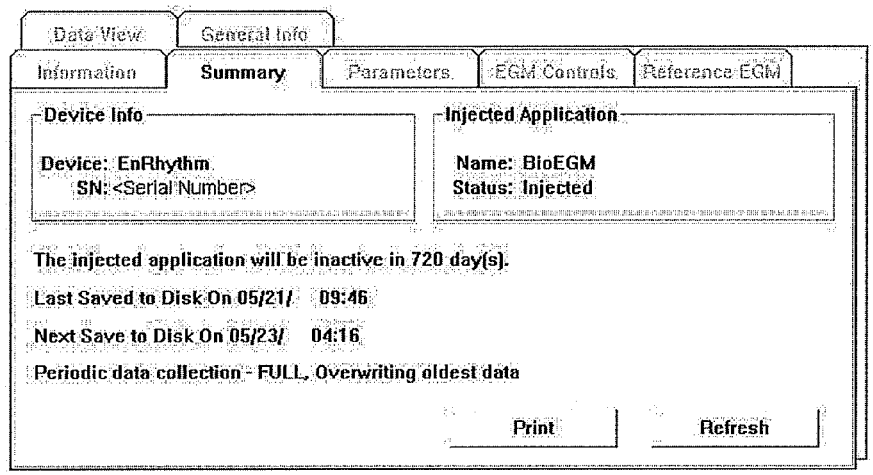

A general overview of User Interface Indicators is shown in FIG. 2A. "Study Duration time remaining" is the indicator displaying the remaining days left of the study before self deactivation. "Next interrogation on" is the indicator providing feedback to the user regarding date for the next interrogation. "Last Interrogation" is the indicator providing feedback to the user regarding the date and time of last interrogation. The date and time indicate the storage capacity based on the chosen data collection parameters. For example, in some applications, if data is collected every hour the next interrogation will need to be performed in two days, while if data is collected every other hour, the next interrogation will need to be performed in four days. If the time/date has passed and the memory has not been cleared, the BioEGM will either overwrite the earliest data or ignore new data, based on the option selected in the Overwrite Data Yes/No of the Parameters Tab shown in FIG. 3. FIGS. 2B and 2C are more detailed screen shots, showing what one would see during the implementation of BioEGM. The Summary screen shot in FIG. 2B shows how many records (or periodic EGMs) have been collected and how many the device is capable of collecting based on available memory. In FIG. 2C, the date for the next save to disk has passed and periodic data collection is full. As a result, the program is overwriting the oldest data.

Periodic Mode Controls

Figure 3:
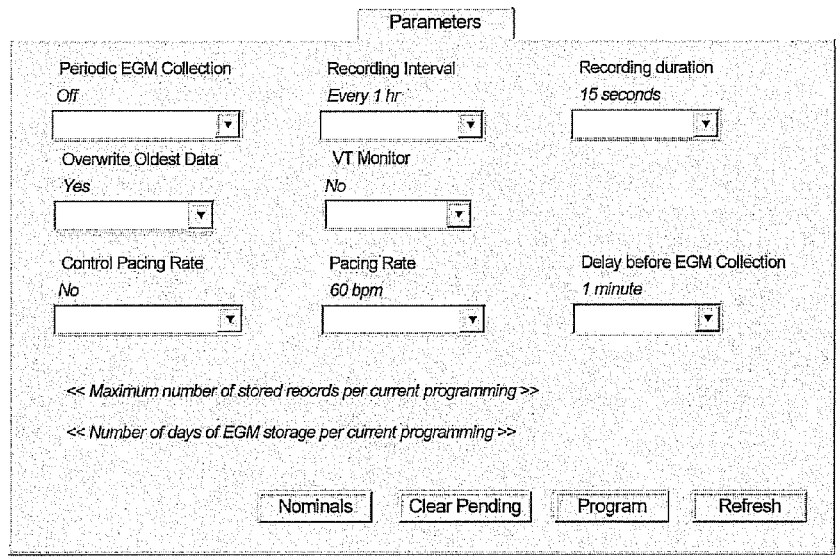
FIG. 3. Screen shot of the Parameters tab in BioEGM.
Figure 4:
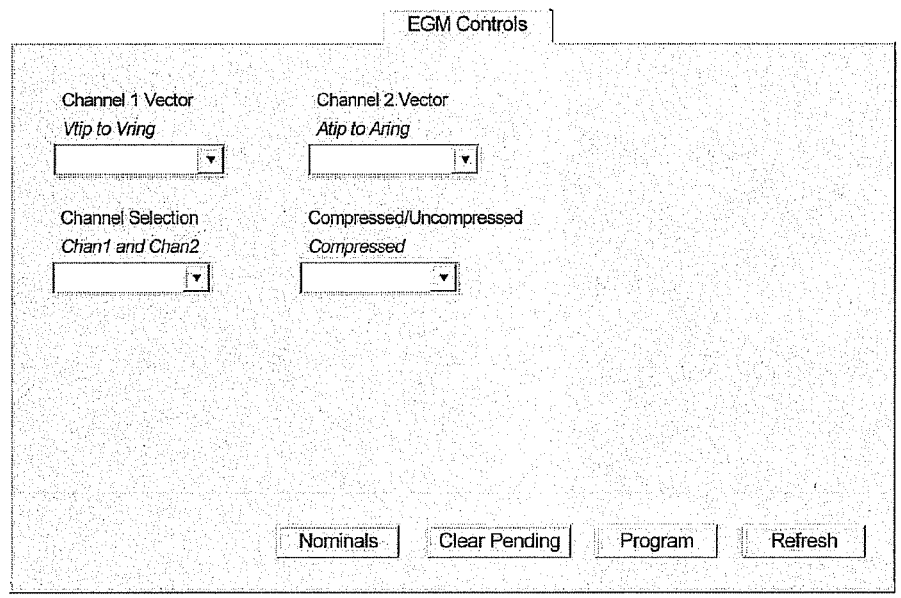
FIG. 4. Screen shot of the EGM Controls tab in BioEGM.
Figure 5:
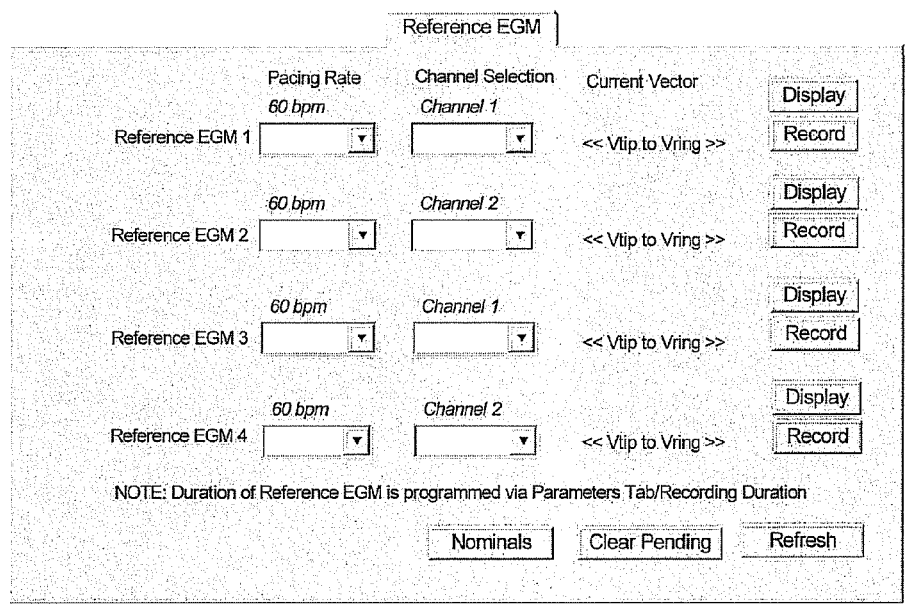
FIG. 5. Screen shot of the Reference EGM tab in BioEGM.

The Bio-pacemaker EGM User Interface allows interactive setting of the parameters shown in FIG. 3, FIG. 4, and FIG. 5, to the ranges indicated in the text describing the parameters. The EnRhythm device captures EGM data using a 2:1 turning point compression algorithm in the EGM buffers (with compression turned off, and 4:1 with compression turned on) and uncompressed EGM in the Morphology buffer. For the purposes of this example, compressed EGM will refer to the device nominal 2:1 turning point compression and uncompressed EGM will refer to the uncompressed EGM collected in the Morphology buffer. It may be desirable to collect both Atrial and Ventricular EGM signals in either the compressed or uncompressed form. Therefore the software allows for the collection of one or two channels of EGM. However if two channels of EGM are collected they will not be of a mixed format (compressed/uncompressed).

Parameters Tab

FIG. 3 shows the Parameters Tab. The parameters tabs allow for the setup of the BioEGM control parameters. These parameters include:

"Periodic Storage ON/OFF." To turn the feature ON or OFF. If the user turns the feature OFF, a confirmation window should pop-up to ensure that feature is not turned OFF inadvertently. When OFF is selected a pop-up window will query for confirmation of "Cancel" or OK", with the message "You have selected to turn the periodic EGM storage feature OFF—Press OK to Confirm." Nominal is OFF.

"Recording duration." Duration for which each EGM record of the intrinsic rhythm would be stored (5, 10 15-180 seconds: at intervals of 15 seconds; nominal is 15 seconds). Since the Recording duration is tied to the Reference data duration, if a change is made there will be a pop-up window with a cautionary statement, such as: "Caution: Recording Duration for periodic data collection is the same duration for the Reference EGM. Changing Recording Duration Invalidates any References BUM collected. Please collect new reference data."

"Interval between recordings." Duration between two consecutive intrinsic rhythm EGMs (15min, 30min, 1hr-12hr at 1hr increments; nominal is 1 hr).

"Overwrite oldest data (Yes/No)." This option will allow the user to decide how the new data will be handled once the memory is full. In the first option the oldest data will be overwritten by the new data. In the second option the new data will be ignored. Nominal is No.

"VT Monitor (Yes/No)." Turn on Device VT monitor mode. When VT monitoring is enable one maximum size EGM data record will be reserved for EGM and Marker Data. Nominal is No.

"Control Pacing (Yes/No)." This option allows for the control of pacing on a beat by beat basis to support high rate pacing. Nominal is No.

"Pacing Rate." Pacing Rate in beats per minute (bpm). Nominal is 60 bpm (range is 30-400 bpm in increments of 10 bpm).

"Delay Before EGM Collection." When Control Pacing is Yes, this allows for the pacing to be turned off for a period of time before the EGM collection is to start. Nominal is 1 minute (range is 0-3 minutes in increments of 15 sec).

"Maximum number of stored episodes." This indicator displays the maximum possible number of EGM records that can be stored by the device based on the available memory and the settings of Recording duration, Interval between recordings, and number of EGM channels to store.

"Number of days of EGM storage." This indicator displays the number of days for which the data can be stored without loss of data based on the programmed EGM control settings.

In order to obtain immediate feedback on changing a parameter; it is desirable for the messages indicating the maximum number of stored records and number of days of EGM storage to be updated if a parameter change is selected and not programmed; or if no parameter selection is made, the current values as calculated from the programmed parameter value. The following buttons assist with this.

"Nominals Button." Selecting this button sets the nominals for each field.

"Clear Pending Button." Selecting Clear Pending resets all parameters.

"Program Button." Selecting Program programs the current values to the device memory.

"Refresh Button." Selecting Refresh re--reads the device and displays the current values.

EGM Controls

The EGM Controls Tab shown in FIG. 4 provides for the setup of the desired EGM type and Vector to be controlled. Specifically:

"Channel 1 Vector" and "Channel 2 Vector" allow for the selection of the vector from which the EGM collection will originate. (Vtip to Vring, Atip to Vring, Atip to Aring, Aring to Vring). Nominal setting is Channel 1-Vtip to Vring; Channel 2-Atip to Aring.

"Compressed or Uncompressed." This parameter allows the collection of one or two channels of compressed or uncompressed EGM.

"Channel Selection." This allows for the choice of Channel 1 Vector, Channel 2 Vector or Channel 1 & Channel 2 vectors from which to collect EGM.

"Nominals Button." Selecting this button sets the nominals for each field.

"Clear Pending Button." Selecting Clear Pending resets all parameters.

"Program Button." Selecting Program programs the current values to the device memory.

"Refresh Button." Selecting Refresh re-reads the device and displays the current values.

Record References

FIG. 5 shows the reference BUM Tabs. This feature provides for the recording of EGM Reference records of paced rhythms at the site of gene/cell injection. The following controls provide for this feature. Specifically, Reference BUM tab include the following: "Pacing rate." Pacing rate for reference selected Nominal is 60 bpm. (range is 30-400 bpm in increments of 10 bpm).

"Channel Selection." This provides for collection of the reference from either Channel 1 or Channel 2 as setup on the parameters tab.

"Current Vector." Vtip to Vring, Atip to Vring, Atip to Aring, Aring to Vring. The message is tied to the programmed value of Channel x vector from the EGM controls Tab.

"Record Button." If Reference Data Field contains Valid Data a warning message would be displayed regarding overwrite.

"Display Button." If there is valid data in the record, selecting the Display button opens up a window and displays the BUM record for the reference. Note that the duration of the Reference BUM is tied to the recording duration of the periodic BUM samples programmed on the parameters tab.

Data View Tab

Figures 6, 7:
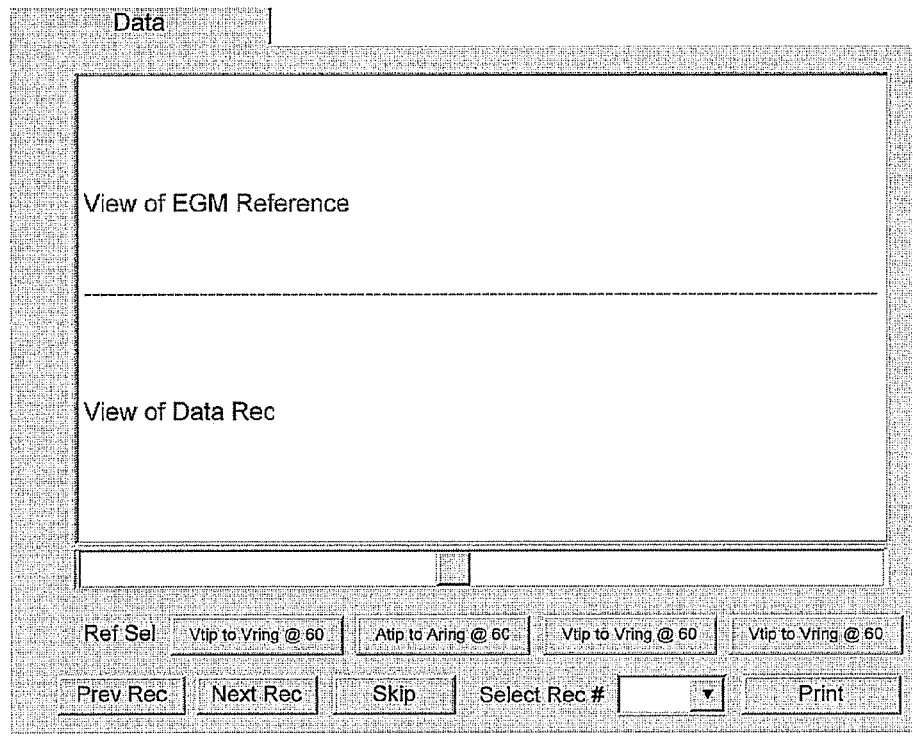
FIG. 6. Screen shot of the Data View tab in BioEGM.
FIG. 7. Screen shot of the General Information tab in BioEGM.

The Bio-pacemaker EGM User Interface provides for viewing of the reference EGM data versus EGM record data. This is shown in FIG. 6. Specifically, Reference Data tab include the following:

"Ref Sel Buttons." Selecting one of the four reference view buttons plots the collected reference EGM in the display window. In some applications, it is desirable to display the vector represented by Ref 1-4 (i.e. Vtip to Vring) on the Reference selection buttons.

"Prey Rec/Next Rec Button." Selecting displays the data record previous or next to, the current record being displayed. In some applications, it is desirable to display the vector from which the EGM record originated so the proper reference can be selected.

"Select Rec # Button." This pull down window provides for the selection of a specific valid record in the buffer.

"Print Button." Selecting print prints the viewed Ref EGM to the programmers strip chart.

General Information Tab

The Bio-pacemaker EGM RAMware and User Interface provides a means of collecting and saving general information about the animal in which the BioEGM RAMware is injected. This provides for identification on reports and saved data. This is shown in FIG. 7. The General Information tab includes the following:

"Clear All Button." Selecting Clear All resets all parameters.

"Program Button." Selecting Program programs the current values to the device memory.

"Refresh Button." Selecting Refresh re-reads the device and displays the current values.

"Print Button." Selecting print prints the parameters to the programmer's strip chart.

RAMware Injection and Removal

The Bio-pacemaker EGM User Interface gives the user the ability to inject the RAMware for Biopacemaker EGM Therapy via user selection. The user interface ensures that the devices used with the RAMware are only the intended devices. The RAMware injection takes place unless there is RAMware present in the device that cannot be identified as compatible with Bio-pacemaker EGM RAMware. The interface gives feedback to the user on the success or failure of the RAMware injection.

The Bio-pacemaker EGM User Interface provides the user the ability to remove the Bio-pacemaker EGM RAMware from the device. The interface gives feedback to the user on the success or failure of the RAMware removal. The device operates according to the standard permanent parameter programming following RAMware removal.

The Bio-pacemaker EGM User Interface only manipulates Bio-pacemaker EGM RAMware. Biopacemaker EGM RAMware is not required to be compatible for injection with any other research RAMware but should be compatible with any RAMware that is an official part of the system undergoing injection.

User Interface Checks

The user interface checks for Elective Replacement Indicator (ERI) and if so indicated, does not allow the device to be used in the study.

Device Interactions

Among the various EnRhythm features, cardiac compass is the only one that must be preserved. However, for initial experiments it is sufficient to have 6-8 weeks of cardiac compass data versus 14 months available in the default mode. A memory to store ~10 episodes should be sufficient to maintain some ability to monitor, detect and store arrhythmias (especially ventricular). Due to the additional battery drain placed on the device because of EGM collection and high rate pacing, the RAMware deactivates itself when ERI is reached, so as not to lose any data.

Bio-Pacemaker EGM Operating Environment Validation

The operating environment of the RAMware is executable RAM memory of the device in which it resides and the time over which it is allowed to operate. To limit the exposure of the RAMware being left active in the device the RAMware residency in the device is limited by the RAMware itself. To limit the potential hazards caused by corruption of RAMware memory, the memory integrity is tested periodically.

RAMware Residency Limit

With some applications, the Bio-pacemaker EGM RAMware may be limited to two years of active operation from the time of injection into the device. When the RAMware has been resident beyond the limit, the RAMware disables all therapy and diagnostic functions. It is not required that a therapy sequence in progress be stopped at the time the lifetime ends, termination of RAMware residency at the end of the current sequence is acceptable. Diagnostic data recorded by the RAMware is retained.

RAMware Memory Integrity Testing

Because the functionality created by RAMware may be altered to unsafe modes of operation due to memory errors, the RAMware performs self-monitoring such that corruption of the memory in which RAMware resides results in a Power-On Reset of the device and thus, the removal of RAMware from memory residency. The memory integrity testing is at least as frequent as the standard firmware memory corruption checking. Normally this is automatic given the design of the RAMware hooks in the firmware and the location of code in parity checked memory. However, if the implementation requires usage of memory outside of these areas, similarly robust protection against corruption then falls on the RAMware requirements. This can't be obtained without locating at least the integrity testing portions in the firmware-provided RAMware memory.

Bio-Pacemaker EGM Diagnostic Data Collection

In order to understand the application of biologics therapy, custom diagnostic functionality is required. The diagnostics will capture the normal sinus/intrinsic rhythm EGM and associated data.

Data Storage Memory Availability

The number of records for each type of diagnostic data storage is determined by the constraint on available memory in the standard EnRhythm. It is not the intent of the design to require disabling of any standard EnRhythm memory usage however tradeoffs may be considered.

Save to Disk Content

Since the diagnostic data providing detailed views requires additional user interface development, detailed data collection needs to be made available for off-line review. This is accomplished by saving the data to a diskette for further processing by tools that do not have to run on the programmer.

The Bio-pacemaker EGM User Interface application provides the user with the ability to save, at a minimum, the Bio-pacemaker EGM specific data to a diskette. This minimum data is defined as the complete operating parameters of the Bio-pacemaker EGM RAMware and all diagnostic data stored by Bio-pacemaker EGM RAMware. In addition, data identifying the Bio-pacemaker EGM RAMware revision, the device serial number, and both the programmer and device date and time are saved. When the Save to Disk operation is performed a print report containing the study information and general information is provided.

Printed Reports

The Bio-pacemaker EGM User Interface application prints information on the 2090 programmer strip chart paper following successful injection of Bio-pacemaker EGM RAMware to generate a Bio-pacemaker EGM General Information Report. The content of this report includes, but is not limited to, device model, serial number, date/time, software title and revision level, copyright, study #, animal #, animal species, device implant date, biologics injection date, Lead #1 Model, lead #1 Serial Number, Lead #1 Implant Date, Lead #1 Position, Lead #2 Model, Lead #2 Serial Number, Lead #2 Implant Date, and Lead #2 Position.

Data Translation Tool

In order to study the details of the diagnostic data collection, a stand-alone tool for translating the data saved by the Bio-pacemaker EGM User Interface into an accessible format for analysis is included. This reduces the burden of the software development for the UI for information that is not time-critical. The Data Translation Tool translates the file saved by the Bio-pacemaker EGM User Interface from the binary format to an ASCII text file in a standard format for parsing. At a minimum, the translated output provides for translating the information from the minimum save to disk data.

Example 2

Creating a Ventricular Biopacemaker

In this example, a gene construct of wild-type HCN4 packaged in a bicistronic adenoviral vector co-expressing GFP demonstrated ventricular biological pacemaker. Briefly, in an AV-blocked canine, a bicistronic adenoviral vector construct (Ad-HCN4-IRES-eGFP) encoding human wild-type HCN4 and eGFP was injected at the apex of the left ventricle (LV). The reporter gene construct Ad-eGFP was also injected at the base of the LV. Periodic in-life data showed ventricular escape rate at 136.2 ±7.0 bpm on Day 3, and the maximum rate achieved was 159.4 bpm at Day 3.4. The similarities in the electrogram morphologies of paced references recorded at the injection procedure and periodic recordings from BioEGM suggest that the origin of activation is at or near the injection sites in the left ventricle. A terminal procedure was performed on Day 7 during which activation mapping confirmed activation from the injection site in the LV apex. Histological analysis of tissue at the injection site was positive for the detection of HCN4 and eGFP gene expression.

Materials and Methods

All experimental in vivo procedures and protocols used in this study were reviewed and approved by the Medtronic PRL Institutional Animal Care and Use Committee. All animal procedures were conducted according to the *Guide for the Care and Use of Laboratory Animals* [DHEW(DHHS) publication (NIH) No. 85-23, revised 1996.]

Complete Heart Block Model and Injection Procedure. On Day 0, a recovery injection procedure was performed on a 33.4 kg male dog. Using a MarinR ablation catheter in the right atrium (RA), the His potential was mapped and radiofrequency ablation was performed to achieve complete heart block. Back-up pacing and sensing was provided by Medtronic Model 5076 leads in the apex of right ventricle (RV) and the RA. A left thoracotomy was made to facilitate epicardial injections in the left ventricle. All injections were performed under Biosafety Level 2 precautions Ad-HCN4-IRES-eGFP ($1.3 \times 10^{10}$ pfu) was injected intramyocardially at the LV apex, and the control construct Ad-eGFP ($8.7 \times 10^8$ pfu) was similarly injected at the LV base. Following the injections, residual virus from the syringe was tested in vitro and found to be functional. An S60 U-clip (Medtronic) was placed at each injection site to mark its location.

Figure 8:
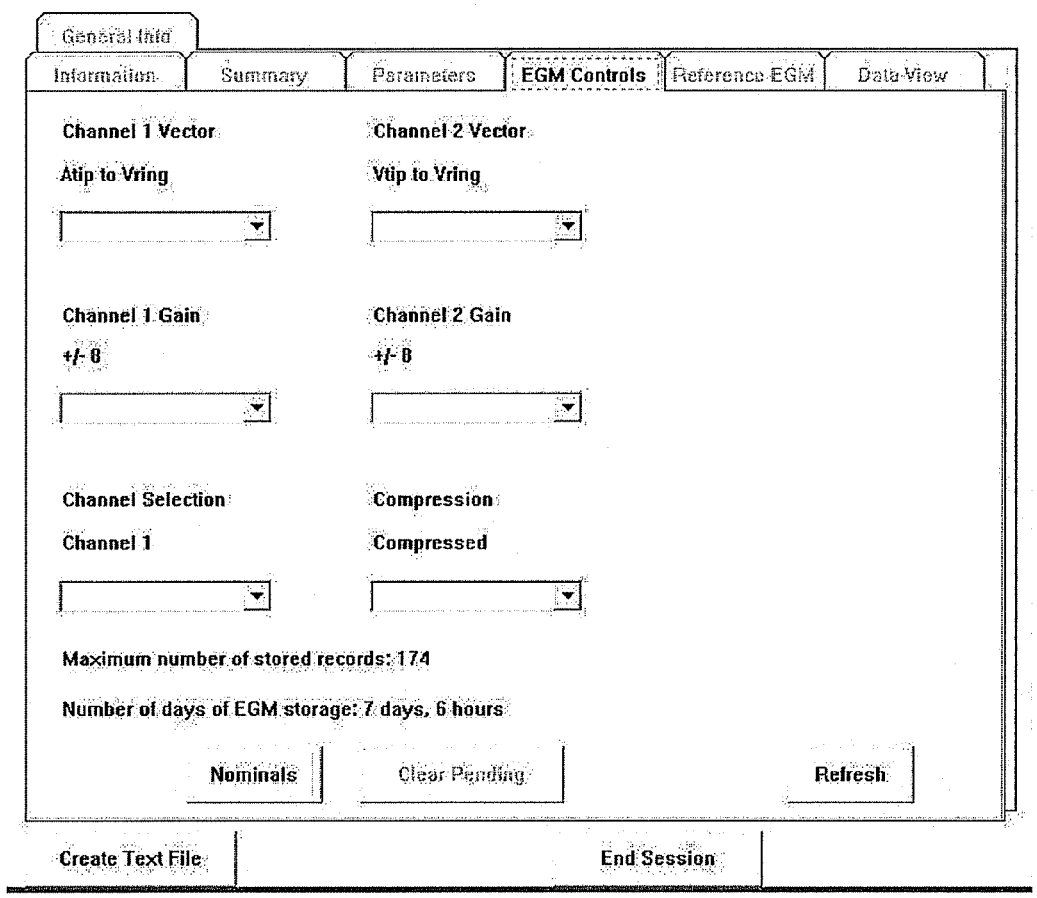
FIG. 8. Screen shot of the EGM Controls tab in BioEGM showing channel vector selection, gain, and compression mode.

Following the injections, the RA and RV leads were tunneled and connected to an EnRhythm implantable pulse generator containing the BioEGM periodic data collection tool. The EGM Controls were programmed as shown in FIG. 8. Specifically, the Channel 1 and 2 vectors were set to record from Vtip to Vring and Atip to Vring, respectively. However, the device was programmed to record only Atip to Vring. The gain was set at ±8 for both channels, and the compressed data format was chosen to increase storage capability.

Reference 1, 3, and 4 electrograms (EGM) were recorded in BioEGM while pacing at 70 bpm with an external pulse generator and MarinR electrophysiological catheter at or near the apical injection site. Because the animal was pacer dependent at the injection procedure, the baseline intrinsic ventricular escape BUM was recorded while the animal was in recovery. Because pacing was facilitated from an external pulse generator for recording of references, the pacing rate in BioEGM was set to the default minimum of 30 bpm. FIG. 9 is a screen shot of the Reference EGM tab of the BioEGM Data Translation Tool showing the programmed settings. Program settings shown include pacing rate, channel selection, and vector. The Translation Tool allows the user to Display the reference electrogram, while the Acquisition tool allows the additional functionality of recording reference EGMs.

BioEGM was further programmed as shown in the Parameters tab, FIG. 10. The Parameters tab from BioEGM includes settings for periodic data collection and back-up pacing. In the event that device memory is exceeded, oldest data was not overwritten; rather, additional data was not stored. The ventricular tachycardia (VT) monitoring capability of the EnRhythm device was disabled to allow greater storage capacity of periodic EGMs. In summary, periodic electrograms were to be collecting every hour for 15 seconds. The recording duration of 15 seconds applied to the collection of references as well as periodic EGMs. Back-up pacing was enabled at a rate of 40 bpm in BioEGM; however, the device defaulted to the higher rate of 70 bpm as programmed in the regular EnRhythm software. Back-up pacing was disabled 60 seconds prior to collecting EGM.

In-Life Monitors and BioEGM. On Days 2 and 6 after recovery, awake monitors were performed to download and clear saved periodic data from device memory, as well as to obtain surface ECG and EGMs in Biopac utilizing standard EnRhythm software. Isoproterenol, a sympathomimetic agonist, was delivered at both monitors to elicit an escape rhythm, if one was not present, and determine responsiveness to neurohormonal stimulation.

Terminal Procedure. A terminal procedure was conducted on Day 7. Activation mapping was performed whereby a stationary electrode pair was placed at the apical injection site and a MarinR catheter was moved to multiple locations on the LV free wall. ECG as well as electrograms from the LV electrode pair, LV catheter, and the RV lead were recorded. Using the EnSite 3000 System (Endocardial Solutions Inc.), dynamic endocardial isopotential maps were created during the escape rhythm as well as pacing from the right ventricle and from the heart wires on the left ventricle. The animal was then euthanized.

Necropsy and Histology. The injection site tissues were harvested at the necropsy. The basal site was formalin fixed and then cute in layers from epi- to endocardium. The apical site was cut in half directly over the U-clips. Half was embedded in OCT and flash frozen; the other half was fixed in formalin and then cut in layers from epicardium to endocardium. Tissue staining and histological analysis was performed. Select levels from each sample were cut at 4 µm every 50 µm. Basal sections were labeled with polyclonal rabbit anti-GFP and VIP substrate, and apical sections were double-stained with anti-GFP and anti-HCN4. To detect apoptotic cells at the LV apical test injection site, a TUNEL assay was performed on the paraffin tissue sections using an apoptosis detection kit (#TA100, R&D Systems, Minneapolis, Minn.). The TUNEL assay provides histological localization of the apoptotic cells by detection of DNA fragmentation using the terminal deoxynucleotidyl transferase enzyme (TdT) to label the free 3'OH ends of the fragments.

Results

In-Life Monitors and BioEGM. During both monitors, A-V dissociation was confirmed and R waves were inverted, indicating the escape beat was originating in the left ventricle.

Ventricular rate averaged 110±1.6 bpm on the Day 2 monitor with no change in heart rate after multiple boluses of isoproterenol (0.25-0.5 µg/kg). The animal was pacer-dependent on the Day 6 monitor, and the escape beat was elicited with one bolus of isoproterenol (0.5 µg/kg).

Figure 11A:
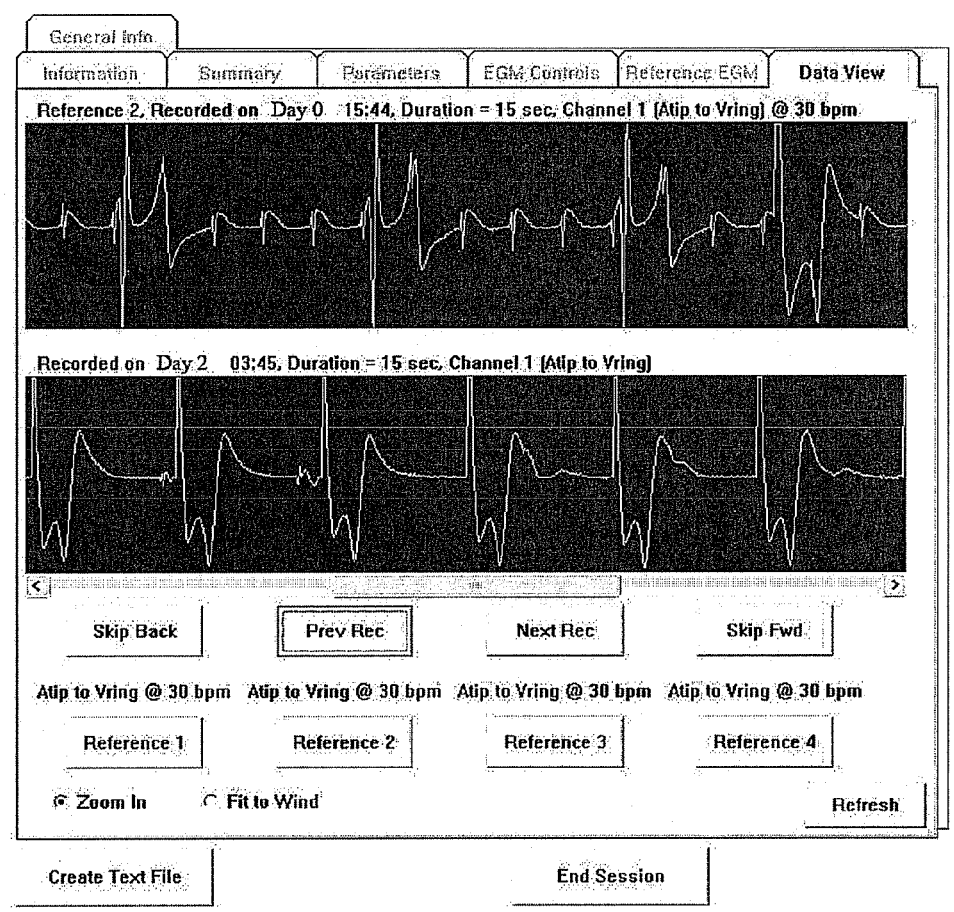
FIG. 11A is a Data View Screen shot for Reference 2 and periodic EGM on Day 2.
Figure 11B:
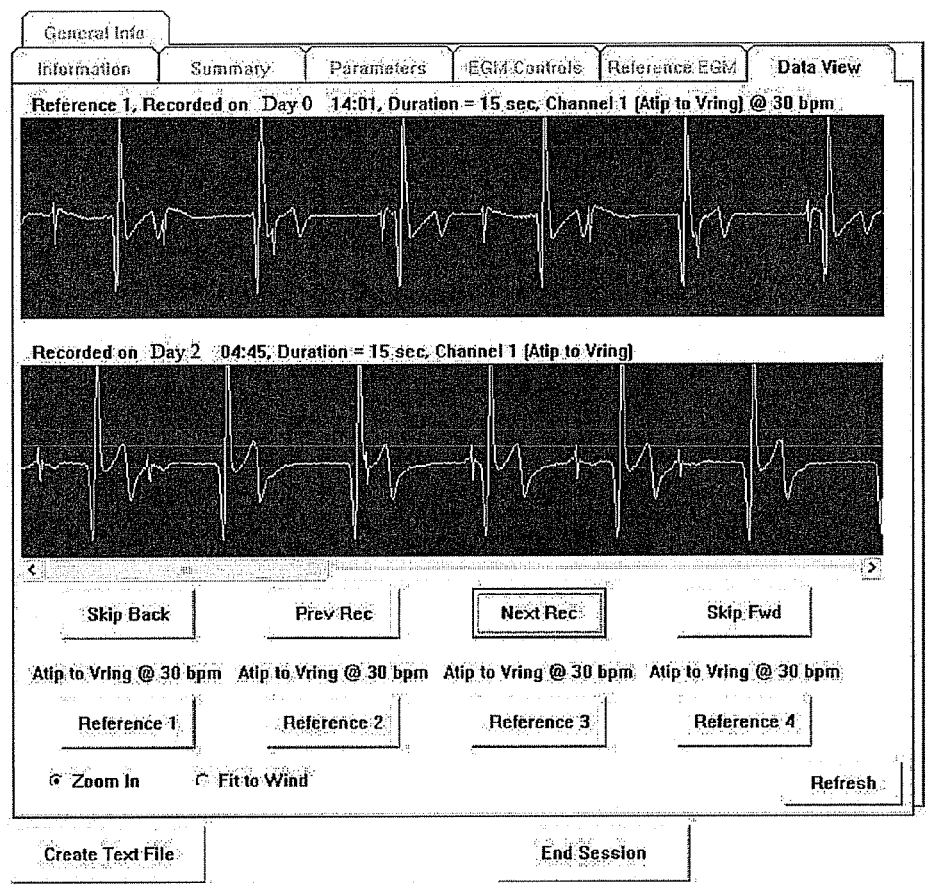
FIG. 11B is a Data View Screen shot for Reference 1 and periodic EGM one hour later.
Figure 11C:
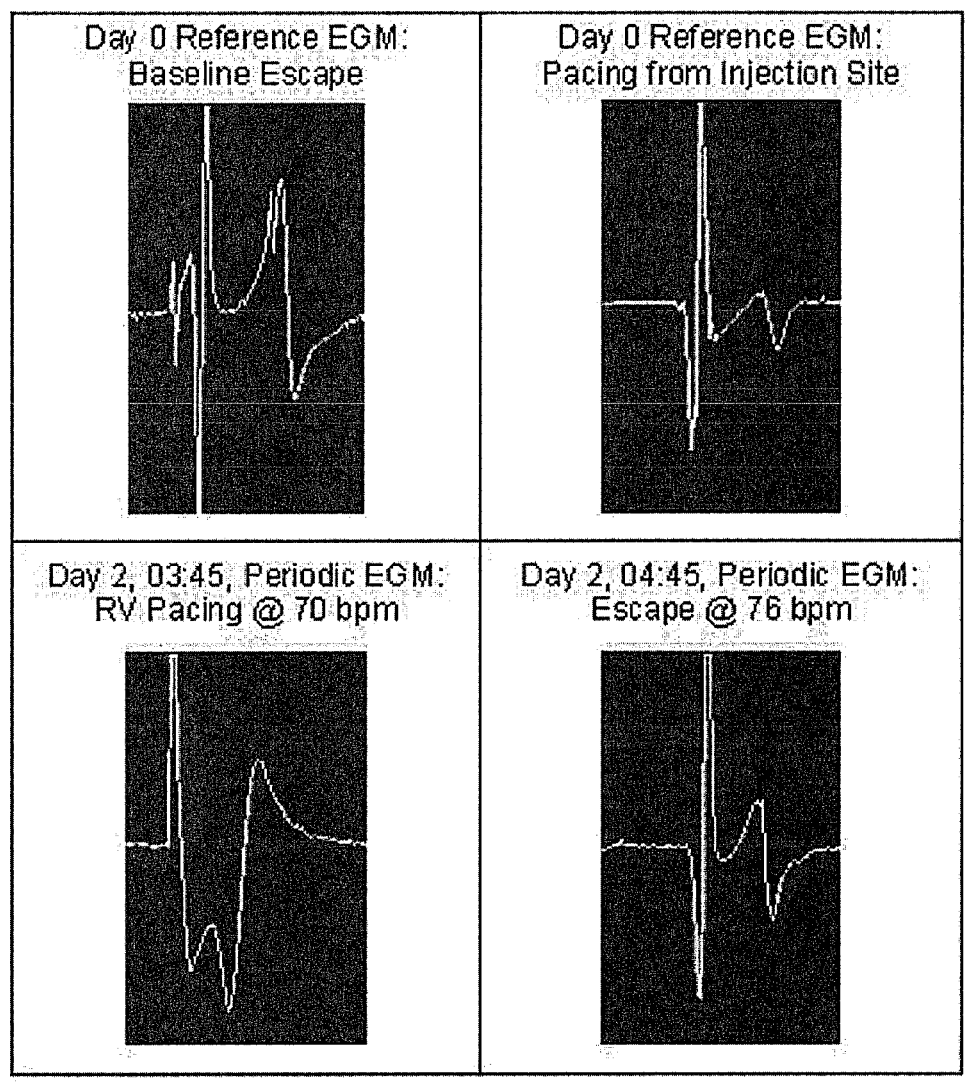
FIG. 11C presents a single beat from each reference and periodic in FIG. 11A and FIG. 11B.

Representative reference and periodic electrogram data recorded in BioEGM are shown in FIG. 11A-C. Electrograms were recorded from the RAtip-RVring vector. Reference EGMs, pacing from the injection sites and the baseline escape, were recorded at the injection procedure on Day 0. Periodic EGMs are representative of the paced and escape morphologies observed in the BioEGM data. The similarities in the EGM morphologies of paced references and periodics suggest that the origin of activation is at or near the injection sites in the left ventricle. Compared to LV-paced references and the periodic escape EGMs, baseline escape shows a positive deflection at the onset of depolarization.

Figure 12:
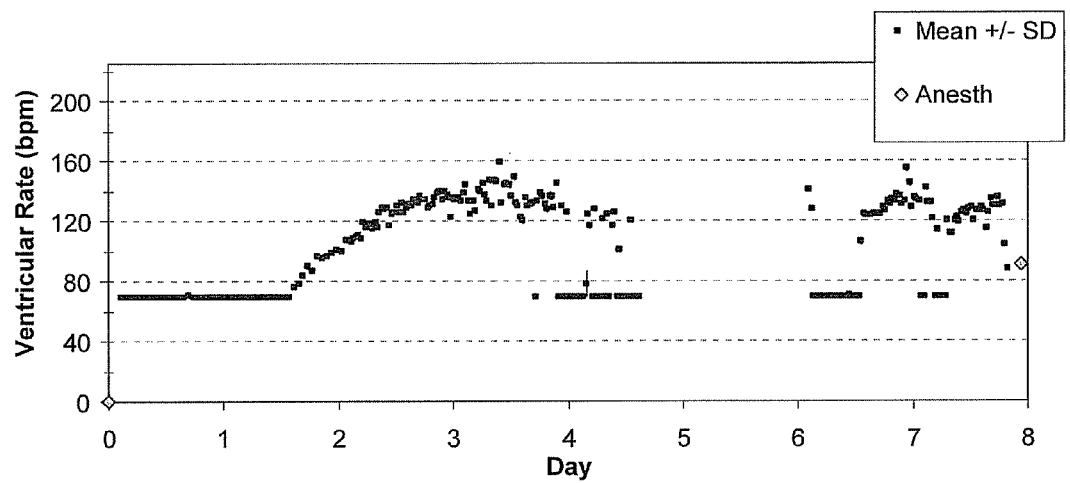
FIG. 12. Ventricular heart rate calculated from periodic BioEGM data. Standard deviation reflects heart rate variability within each 15-second epoch of data. Missing data is a result of the device memory capacity being exceeded.

The average ventricular heart rate and standard deviations for each 15-second epoch of BioEGM data are presented in FIG. 12. Device memory capacity was exceeded and explains the missing data in the figure. During Day 3, the average heart rate from all periodic data was 136.2±7.0 with a maximum of 159.4 bpm. In the 24 hours prior to the terminal procedure, the average rate of escape beats resembling those originating from the injection site was 126.7±14.4 bpm.

Figure 13A:
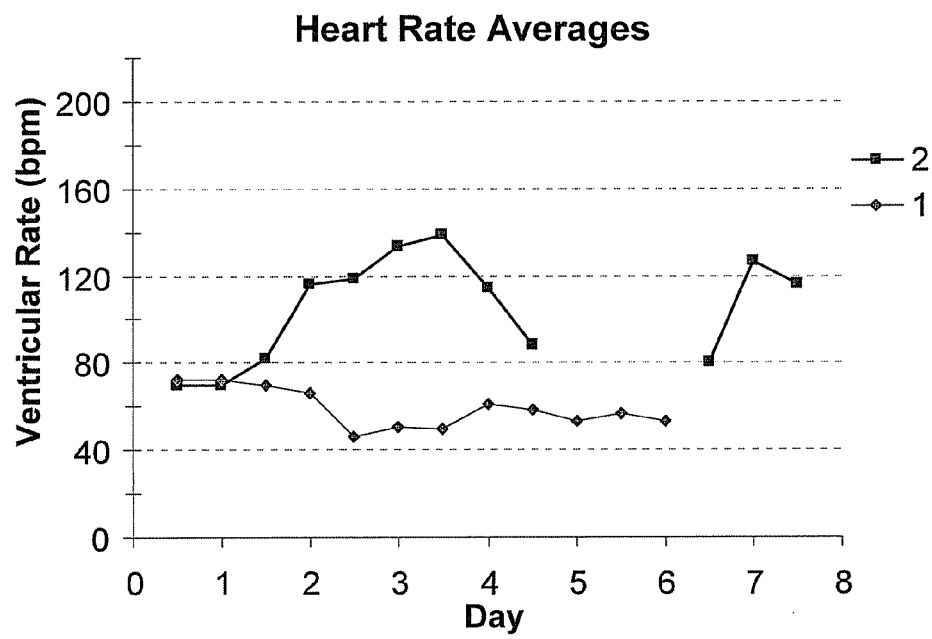
FIG. 13. Heart rate averages (FIG. 13A) and variability (FIG. 13B) over a 12-hour period for Dog 1 (diamond) and Dog 2 (square) calculated from BioEGM.
Figure 13B:
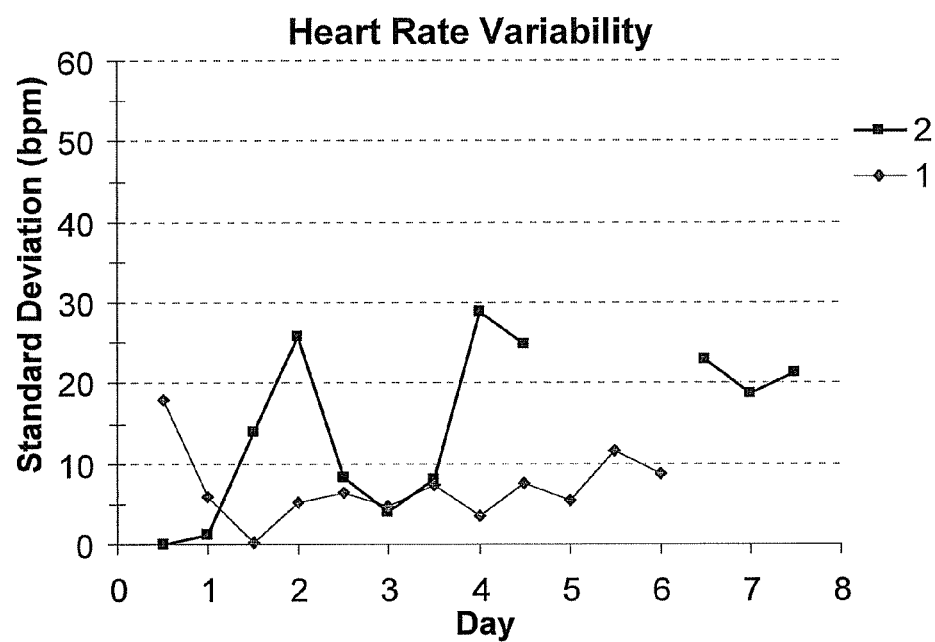

The bi-daily averages from all periodic data are presented in FIG. 13. FIG. 13A is heart rate averages and FIG. 13B is heart rate variability over a 12-hour period for Dog 2 calculated from BioEGM data. Earlier experimental data for Dog 1 are included for reference. In Dog 1, the bicistronic adenoviral vector encoding human wild-type HCN4 and eGFP was injected epicardially at two different doses (lower than those used for Dog 2) and sites in the left ventricle. Biological pacemaker function was not observed in vivo, and histological analysis was negative for the detection of GFP or HCN4 proteins at all injection sites.

Terminal Procedure. Heart rate was stable at about 90 bpm and electrocardiogram morphology was consistent throughout traditional and non-contact activation mapping. Both mapping procedures showed the earliest site of activation to be at the LV apical HCN4 injection site.

Tissue Staining and Histological Analysis. Paraffin tissue sections from the LV apical site of Dog 2 with Adv-HCn4-IRES-eGFP were double stained by fluorescently tagged anti-GFP at the injection site and at a remote area on the same slide, and anti-HCN4 at the injection site and at a remote area on the same slide. This staining confirmed expression of test and reporter genes at the LV apical injection site receiving Ad-HCN4-IRES-GFP. In the OCT-embedded tissue samples, HCN4 expression was successfully detected on the cell membrane, but GFP expression was lost due to the OCT method. The double staining of HCN4 and GFP on paraffin tissue sections clearly show co-expression of HCN4 and GFP on the same cells, with GFP expressing in the cytoplasm and HCN4 expressing on the cell membrane. No GFP/HCN4 was found in remote areas of the same slide which presented with positive staining, indicating GFP/HCN4 expression was localized as in the control injections.

Discussion

Ventricular Biological Pacemaker. Less than two days post-injection, the baseline escape rate of <70 bpm began gradually increasing to reach 136.2±7.0 bpm at day 3, 126.7±14.4 bpm for the 24 hours prior to the term procedure, and approximately 90 bpm while anesthetized during the terminal procedure. The true baseline escape rate prior to expression is not known because, although BioEGM was programmed to disable pacing prior to data collection, the regular software of the EnRhythm device dominated at VVI 70 bpm. At the day 6 monitor, the animal was completely electronic pacemaker dependent and isoproterenol was administered to elicit left ventricular automaticity. The instability of expression and increase in standard deviation between days 3 and 6 may be due inflammation elicited by the adenovirus, which would be more pronounced after day 3.

Changes in periodic in-life electrograms as well as mapping data collected at the terminal procedure indicate the increased ventricular rate corresponds to activation from the injection site. Looking first at BioEGM data, compared to the baseline escape which shows a positive deflection at the onset of depolarization, the initial deflection is negative in both injection site paced references and periodic escape EGMs. Similarities between paced and periodic escape beats suggest the origin of activation is at the injection site. Histological data confirm expression of test and reporter genes at the LV apical injection site receiving Ad-HCN4-IBES-GFP. Expression was not detected within the same tissue block remote from the injection site, indicating localized expression.

Example 3

Creating Atrial and Ventricular Biological Pacemakers

Figure 14A:
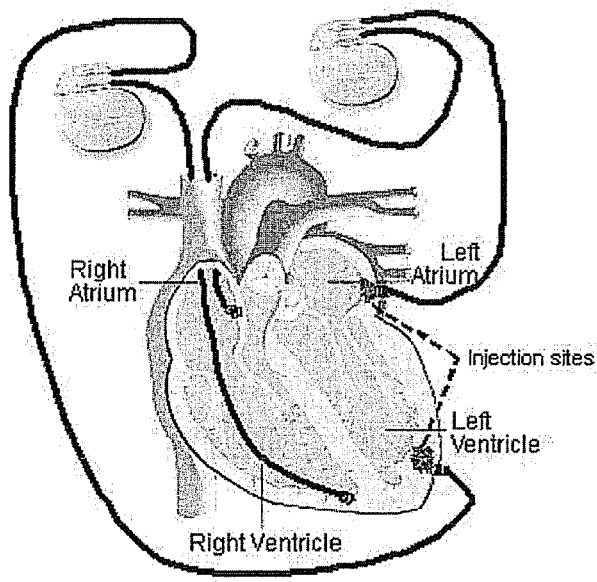
FIG. 14. The location of leads and injections showing ventricular leads connecting to one implantable pulse generator (IPG) and atrial leads to another (FIG. 14A) and reference and periodic electrogram recordings from modified software within the IPGs (FIG. 14B).
Figure 14B:
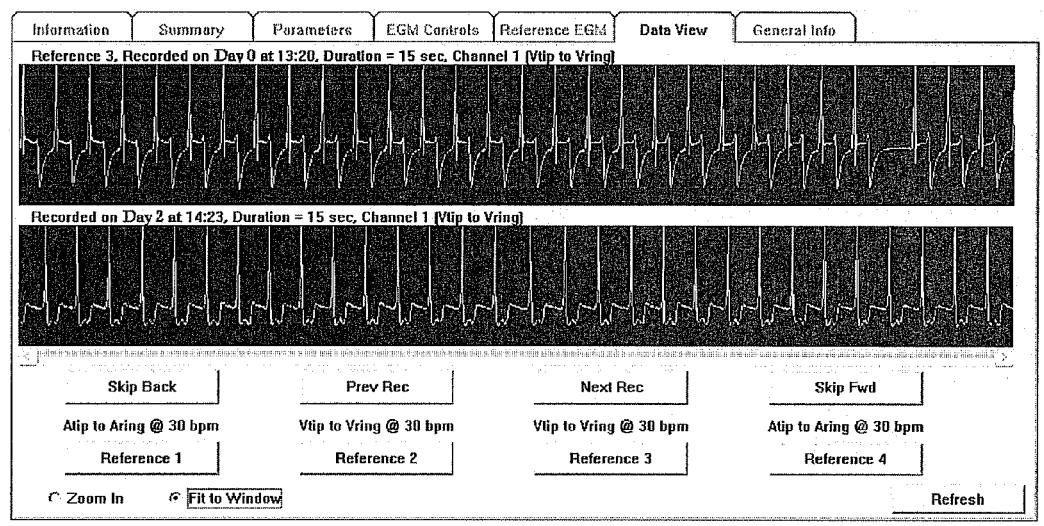

In this example an adenoviral vector encoding a fused construct of truncated HCN4 and eGFP (Ad-HCN4m-eGFP) was injected at the apex of the left ventricle (LV) and at a site in the left atrium (LA) an AV-blocked canine. Leads were implanted at the injection sites as well as in the right atrium and right ventricle, and atrial leads were connected to a modified implantable pulse generator (IPG) and ventricular leads to a second modified IPG (FIG. 14A). At implant, reference electrograms of the escape rhythm and pacing from each injection site were recorded on the IPGs; and for one week, periodic electrograms using two lead vectors were recorded for 15 seconds every 0.5 to 2 hours (FIG. 14B). The periodic data showed isolated beats and short, intermittent runs of left ventricular activation, as well as isolated left atrial beats. At both awake monitors and the terminal procedure, more sustained left ventricular activation was elicited with administration of isoproterenol, a sympathomimetic agonist, and this activity was mapped to the injection site at the terminal procedure. No left atrial activation was observed at the terminal procedure, either with or without vagal stimulation, nor following sinoatrial node ablation resulting in a sinus rate of 40 bpm. Periodic electrograms were of great utility in identifying and characterizing activity of both atrial and ventricular biological pacemakers.

Methods

Complete Heart Block Model and Injection Procedure. All experimental in vivo procedures and protocols used in this study were reviewed and approved by the Medtronic PRL Institutional Animal Care and Use Committee. All animal procedures were conducted according to the *Guide for the Care and Use of Laboratory Animals* [DHEW(DHHS) publication (NIH) No. 85-23, revised 1996.]

A recovery ablation and injection procedure was performed on a 27.65 kg male dog. Pacing leads were implanted in the right ventricle and right atrium. The His signal was mapped with a radiofrequency ablation catheter and ablations performed until complete atrioventricular (AV) block was accomplished. Back-up pacing and sensing was provided by leads implanted in the apex of the right ventricle (RV) and in the right atrium (RA). A left thoracotomy was made to facilitate epicardial injections in the left ventricle (LV) and left atrium (LA). Under Biosafety Level 2 precautions, adenovirus containing modified HCN4 and eGFP fusion construct (Ad-eGFP-HCN4m) was injected at a site in the LV apex as well as in the LA at a dose range of $1.2 \times 10^8$ to $1.2 \times 10^9$ pfu. One lead was placed epicardially at the injection site in each chamber. The left and right atrial leads were connected to the atrial and ventricular ports, respectively, of an EnRhythm device downloaded with the BioEGM periodic data collection tool. The left and right ventricular leads were similarly connected to a second device. (See FIG. 14A)

Figure 15:
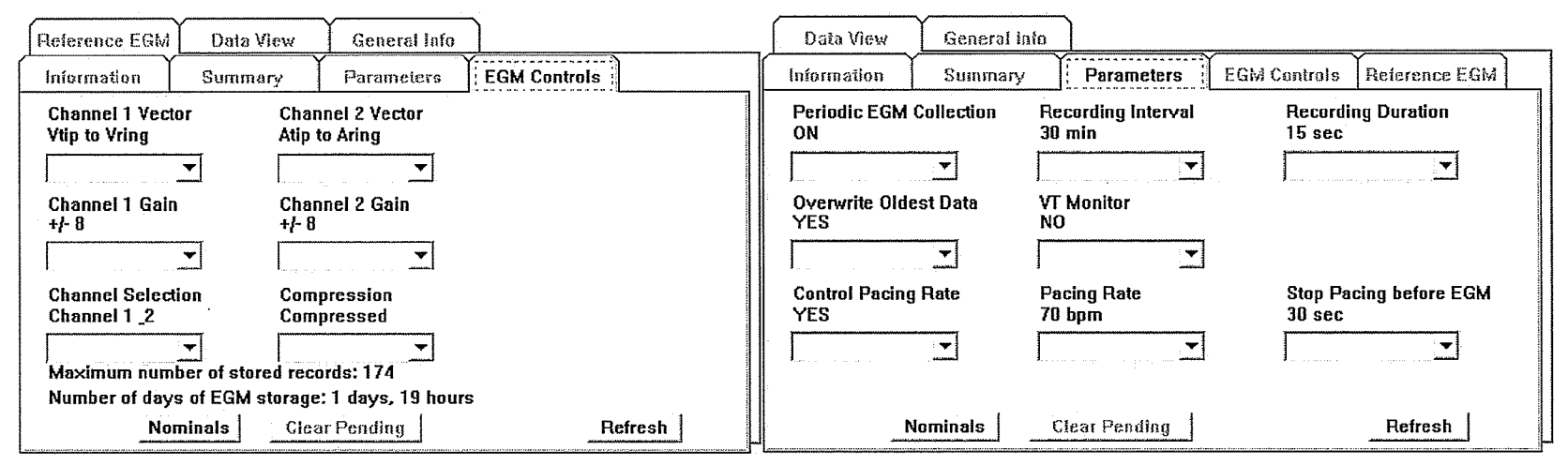

Programming BioEGM Periodic Data Collection Tool. Prior to recording of reference electrograms, the EGM controls and data collection parameters were programmed. Since the left heart leads were connected to the atrial port of the IPG, the Channel 2 vector for recording of electrograms from the left heart leads appear as Atip to Aring, referring to tip and ring electrodes of the atrial lead. Similarly, since the right heart leads were connected to the ventricular port of each IPG, the Channel 1 vector for recording electrograms from the right heart leads appear as Vtip to Vring. The device was programmed to record both Channels 1 and 2. Both channels were set at a gain of ±8 in the ventricular device and ±2 in the atrial device, and the compressed data format was chosen to increase storage capability. In both devices, periodic EGM collection was turned on with a recording interval of 1 hour and duration of 15 sec. After collection of references, the 'control pacing rate' feature was enabled in the ventricular device, but not the atrial device, at a rate of 70 bpm, and pacing was disabled 30 seconds prior to collection of electrograms to allow intrinsic rhythms to recover from overdrive suppression. Screen shots of the "EGM Controls" and "Parameters" tabs of from the ventricular device are contained in FIG. 15. With this combination of parameters, the device memory allows the collection of 174 periodic records to take place over 1 day, 19 hours. The ventricular tachycardia (VT) monitor feature of the IPG was disabled to maximize data storage capacity. If data was not stored and the device memory cleared prior to that point, the device was programmed to overwrite the oldest data.

References of injection site pacing and intrinsic or escape electrograms were captured as summarized in Table 1. For paced references, an electrophysiology (EP) catheter was placed epicardially and pacing delivered from an external pulse generator at the rate listed. In BioEGM, the pacing rates were set at 30 bpm to allow escape beats and pacing from the external source to override. The recording duration for the references matched that selected under the Parameters tab for recording of periodic electrograms. A screen shot of the Reference EGM tab is shown as FIG. 16. The BioEGM Translation Tool allows the user to display the reference electrogram, while the Acquisition tool allows the additional functionality of recording reference EGMs.

TABLE 1

Recording conditions of reference EGMs in modified IPGs.

| Device | Reference | Rate (bpm) | Condition/Site | Recording Channel |
|---|---|---|---|---|
| Ventricular | 1 | 35-40 | Ventricular Escape | Ch 2 (LV) |
| | 2 | 35-40 | Ventricular Escape | Ch 1 (RV) |
| | 3 | 120 | Pace LV apex | Ch 1 (RV) |
| | 4 | 120 | Pace LV apex | Ch 2 (LV) |
| Atrial | 1 | 130 | Atrial Intrinsic | Ch 2 (LA) |
| | 2 | 140 | Pace LA | Ch 2 (LA) |
| | 3 | 140 | Pace LA | Ch 2 (LA) |
| | 4 | 140 | Pace LA | Ch 1 (RA) |

In-Life Monitors. On Days 2 and 6 after recovery, awake, un-anaesthetized monitors were performed to download and clear saved periodic data from device memory, as well as to obtain surface ECG and EGMs in Biopac utilizing standard EnRhythm software. Isoproterenol, a sympathomimetic agonist, was delivered at both monitors to elicit an escape rhythm, if one was not present, and determine responsiveness to neurohormonal stimulation.

Terminal Procedure. Seven days after the injections, a terminal procedure was conducted wherein the chest was opened to facilitate activation mapping across the LV using a grid pattern for identification of the breakout region. Isoproterenol was administered duration activation mapping. To slow sinus node activity and allow for evaluation of left atrial biological pacemaker activity, vagus nerve stimulation and sinus node ablations were performed.

Using the EnSite 3000 System (Endocardial Solutions Inc.), dynamic endocardial isopotential maps of the left ventricle as well as the right atrium were created during the escape/sinus rhythm as well as pacing from the injection sites in the left ventricle and left atrium, respectively, and remote sites on the respective right chambers. The animal was then euthanized.

Necropsy and Histology. The injection site tissues were harvested at necropsy. The LV apical site was cut into two sections. One part was formalin fixed and paraffin embedded, and the remaining tissue was flash frozen in liquid nitrogen for western blot analysis. The LA injection site was formalin fixed and paraffin embedded. All LA and LV paraffin samples were cut at 4 µm every 50 µm and double stained with anti-HCN4 and anti-GFP.

Results

Figure 17:
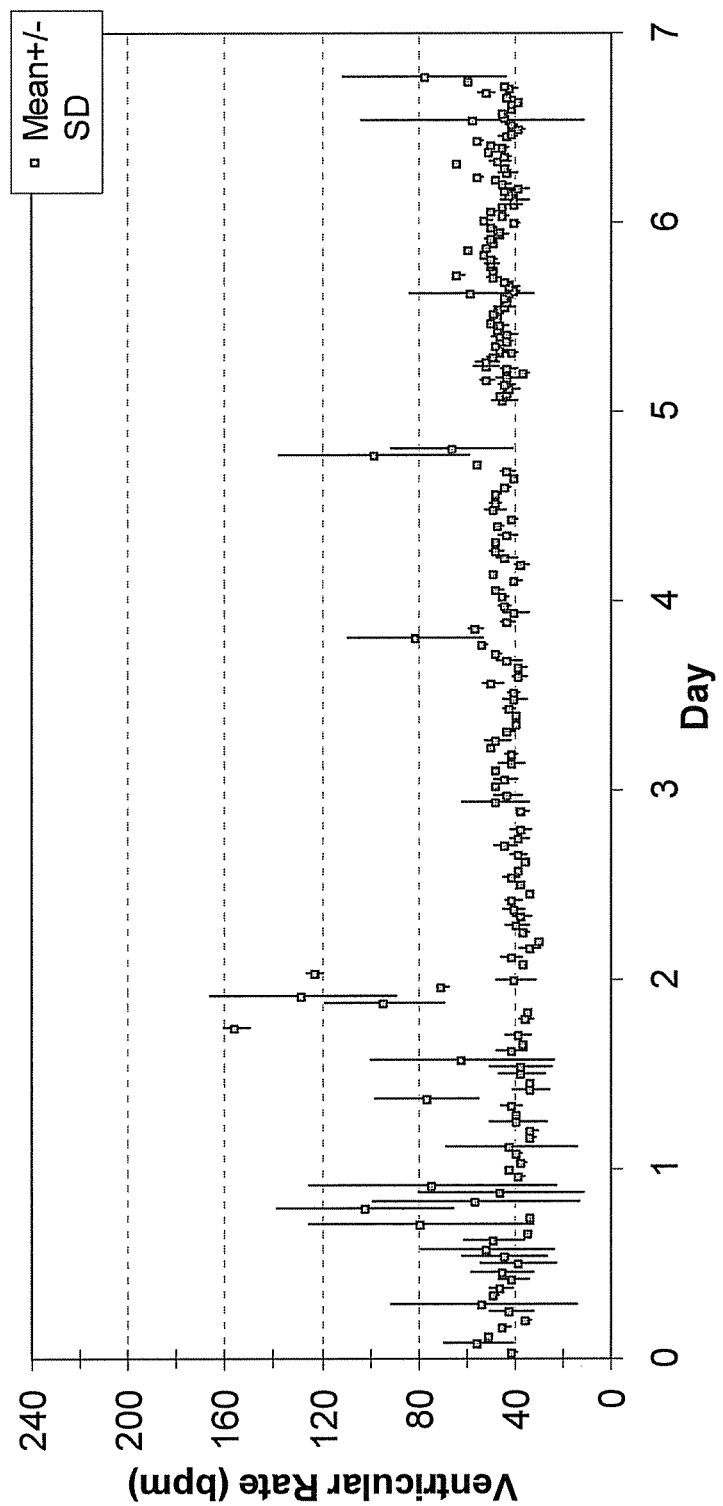
FIG. 17. Ventricular heart rate calculated from periodic BioEGM data. Error bars (standard deviation) reflect heart rate variability within each 15-second epoch of data.
Figure 18A:
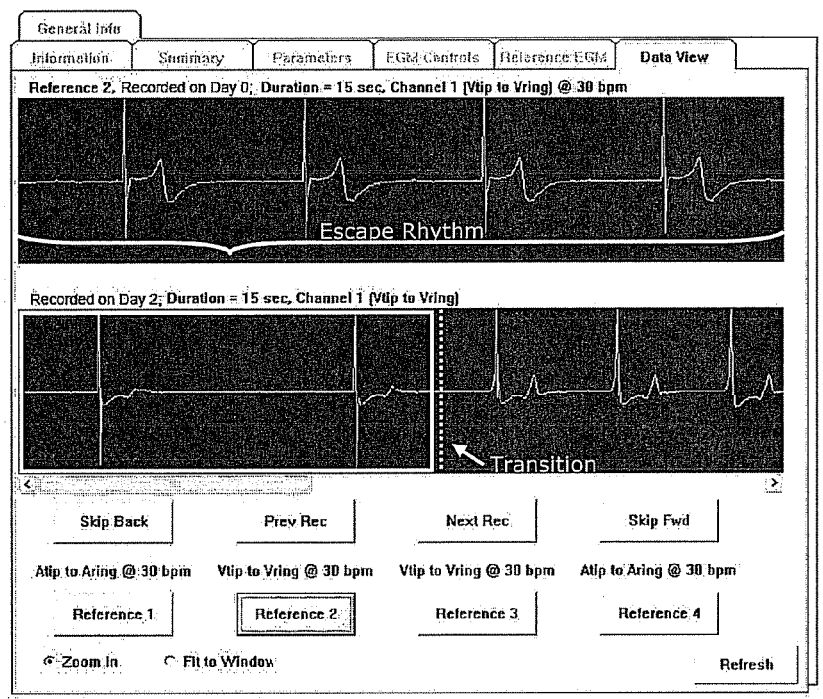
In FIG. 18A, Reference 2 shows electrograms of a ventricular escape rhythm (top panel), similar in morphology to the first two beats in the periodic recording (bottom panel).
Figure 18B:
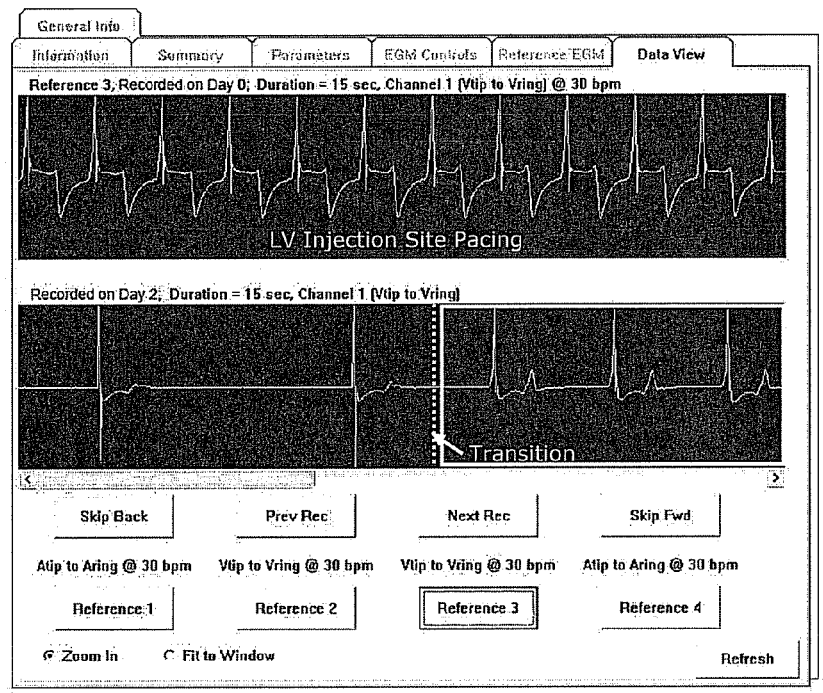
In FIG. 18B, Reference 3 shows electrograms during pacing from the left ventricular injection site (top panel), similar in morphology to the last 3 beats of the periodic recording (bottom panel).
Figure 19A:
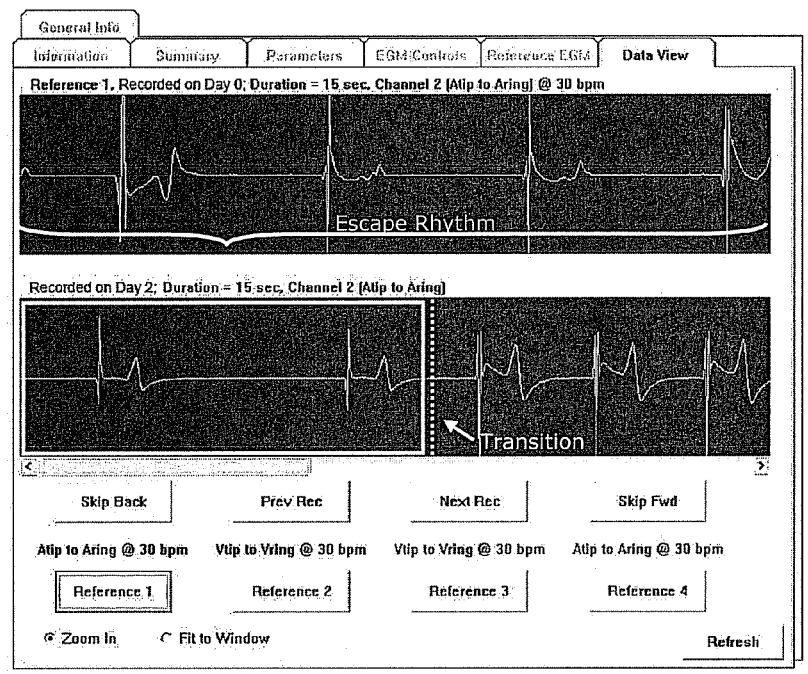
In FIG. 19A, Reference 1 shows electrograms of a ventricular escape rhythm (top panel), similar in morphology to the first two beats in the periodic recording (bottom panel).
Figure 19B:
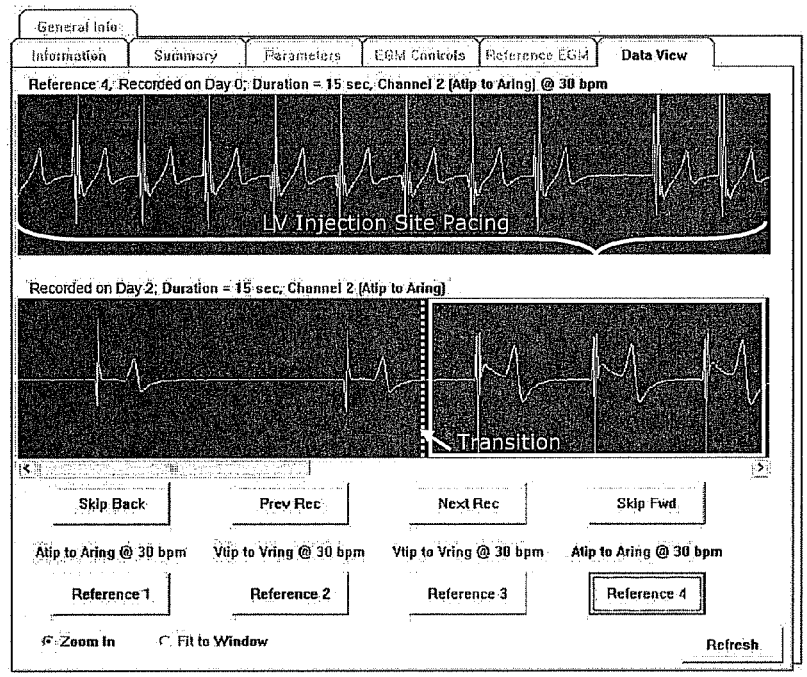
In FIG. 19B, Reference 4 shows electrograms during pacing from the left ventricular injection site (top panel), similar in morphology to the last 3 beats of the periodic recording (bottom panel).
Figure 20:
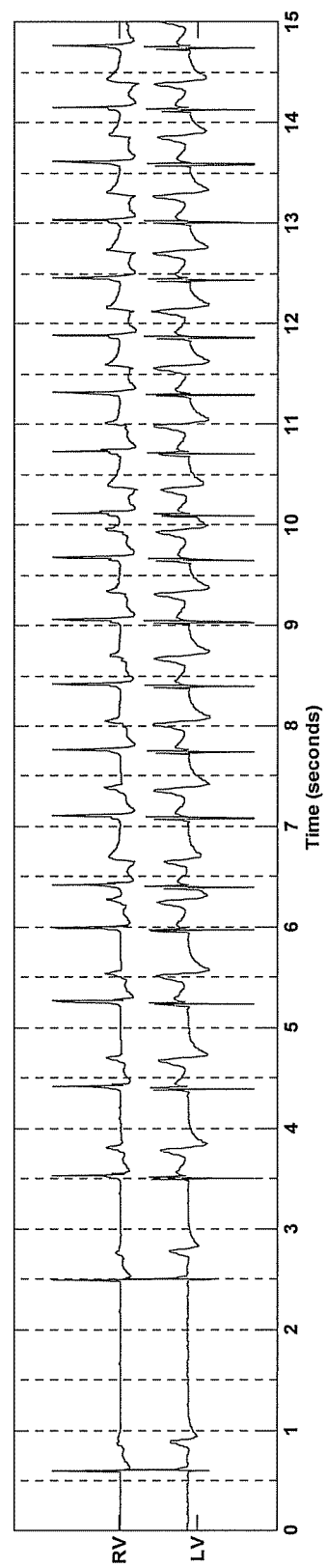
FIG. 20. Periodic electrograms recorded on Day 2 at 10:23 from Channel 1 (RV, top) and Channel 2 (LV, bottom) showing transition from ventricular escape rhythm to biological pacing from the LV. In addition to morphological changes in the EGMs, the LV EGMs precede the RV EGMs from the third beat and beyond in this 15-second epoch of data.

Ventricular Biological Pacemaker. FIG. 17 contains the average ventricular heart rate for each 15-second epoch of BioEGM data showing some heart rate variability on post-operative days 1 and 2. This was primarily due to premature ventricular contractions during recovery. However, starting on Day 2, isolated LV beats or intermittent periods of LV activation were observed. FIG. 18, FIG. 19, and FIG. 20 illustrate the transition from the right ventricular escape rhythm to LV activation, presumably from the injection site, on Day 2.

At the Day 3 monitor, the dog was pacer dependent at VVI 70. With the pacing rate lowered to 30 bpm, the right ventricular escape emerged with isolated runs of LV activation. Bolus administration of isoproterenol elicited consistent LV activation at a rate of >120 bpm which slowly decreased and became intermittent with washout of the drug. At the conclusion of the monitor, and approximately 25 minutes after isoproterenol had been administered, LV activation was intermittent at 75-80 bpm with RV pacing at 70 bpm. Likewise, at the Day 5 monitor, the escape rhythm predominated with pacing disabled, and LV activation was elicited with isoproterenol.

At the terminal procedure, isoproterenol was required to elicit stable left ventricular automaticity at 50 bpm which was mapped to the injection site.

Figure 21A:
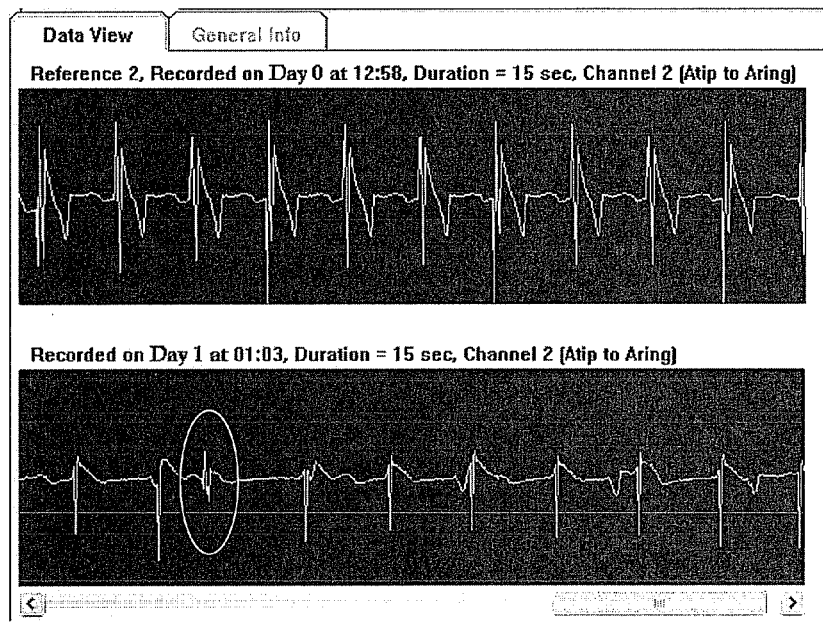
FIG. 21A shows Reference 2 (top panel) shows LA electrograms of pacing from the LA injection site, similar in morphology to the circled beat in the periodic recording (bottom panel), similar in morphology to the circled beat in the periodic recording (bottom panel).
Figure 21B:
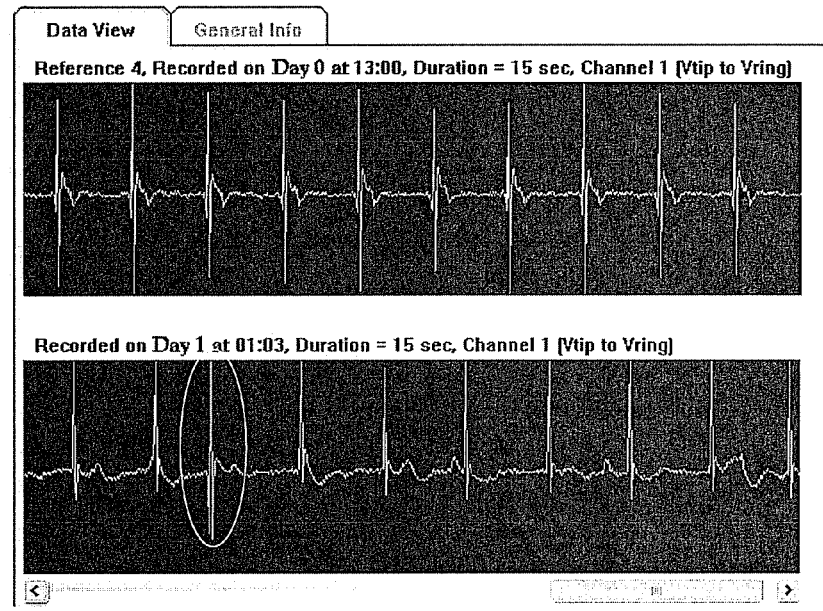
FIG. 21B shows Reference 4 (top) shows RA electrograms during pacing from the LA injection site. Similar to the paced reference, the circled beat in the periodic electrogram in the bottom panel has an initial negative downward deflection indicative of LV activation.
Figure 21C:
As shown in FIG. 21C, plotting simultaneous LA and RA recordings demonstrates LA activation in the third beat, which corresponds to the circled beat in FIG. 21A and FIG. 21B.

Atrial Biological Pacemaker. Isolated beats of LA activation were observed between 12 hours and 4 days post injection. Representative plots are shown in FIG. 21. In addition to change in morphology on Channels 1 and 2 (FIGS. 21A and 21B), simultaneous recording of RA and LA electrograms allowed for determination of the order of activation (FIG. 21C).

At the Day 3 and 5 awake monitors, atrial rate was highly variable throughout, but all observed atrial activity originated from the right side. Biopacemaking activity from the left atrium was not observed at the terminal monitor. Though vagal stimulation and SA node ablation slowed atrial rate to <40 bpm for up to two minutes, the right atrium remained the source of automaticity.

Discussion

Ventricular Biological Pacemaker. Escape rate, rhythm, and ventricle of origin varied during the first two days following injection. Isolated beats and short runs of LV activation were recorded in periodic BioEGM data as well as during awake monitors. Bolus administration of isoproterenol transiently increased rate and stability of the rhythm. At the terminal monitor, isoproterenol was required to elicit left ventricular automaticity that was mapped to the injection site. Since delivery parameters except dose were kept constant, the lower dose of $2.6 \times 10^8$ pfu ($\frac{1}{50}^{th}$ max dose) may not have been sufficient to elicit sustained biological pacemaking activity in the ventricle.

Atrial Biological Pacemaker. Biopacemaking activity from the left atrium was not observed at the terminal monitor. However, isolated left atrial beats were detected in the periodic BioEGM data within 12 hours to 4 days post-injection. Elevated atrial rate in an AV-blocked canine may suppress left atrial biopacemaker activity. Though vagal stimulation and SA node ablation slowed atrial rate to <40 bpm for up to two minutes, the right atrium remained the source of automaticity.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A system for monitoring the functional effect of an intervention effecting cardiac pacing, the system comprising:
   an implantable electronic pulse generator delivering artificial cardiac pacing;
   a means for halting the electronic pulse generator delivering artificial cardiac pacing at predetermined data collection intervals;
   a sensor for obtaining data on one or more intrinsic physiological parameters of cardiac pacing during the predetermined data collection intervals; and
   a computer readable medium programmed with instructions, the instructions comprising:
   instructions for recording and storing reference data for one or more intrinsic physiological parameters of cardiac pacing prior to the intervention effecting cardiac pacing;
   wherein the reference data recorded and stored for one or more intrinsic physiological parameters of cardiac pacing prior to the intervention effecting cardiac pacing comprises a response to artificial cardiac pacing at the intervention site;
   wherein the intervention effecting cardiac pacing comprises gene therapy, cell therapy, ablation, and/or drug delivery;
   instructions for halting the electronic pulse generator delivering artificial cardiac pacing at predetermined data collection intervals after the intervention effecting cardiac pacing; and
   instructions for obtaining data on one or more intrinsic physiological parameters of cardiac pacing during the predetermined data collection interval.

2. The system of claim 1 further comprising an external device that provides:
   instructions for halting the electronic pulse generator delivering artificial cardiac pacing at predetermined data collection intervals; and
   instructions for obtaining data on one or more intrinsic physiological parameters of cardiac pacing during the predetermined data collection intervals.

3. The system of claim 1 further comprising an external device that receives data on the one or more intrinsic physiological parameters of cardiac pacing and presents the data to a user.

4. A system for monitoring the functional effect of an intervention effecting cardiac pacing, the system comprising:
   an implantable medical device (IMD) comprising an electronic pulse generator delivering artificial cardiac pacing, a means of halting the electronic pulse generator delivering artificial cardiac pacing at predetermined data collection intervals, and one or more sensors for obtaining data on one or more intrinsic physiological parameters of cardiac pacing during the predetermined data collection intervals; and
   a computer readable medium programmed with instructions, the instructions comprising:
   instructions for recording and storing reference data for one or more intrinsic physiological parameters of cardiac pacing prior to the intervention effecting cardiac pacing;
   wherein the reference data recorded and stored for one or more intrinsic physiological parameters of cardiac pacing comprises a response to artificial cardiac pacing at the intervention site,
   wherein the intervention effecting cardiac pacing comprises gene therapy, cell therapy, ablation, and/or drug delivery,
   instructions for halting artificial pacing provided by the IMD at predetermined data collection intervals after the intervention effecting cardiac pacing,
   instructions for recording the data on one or more intrinsic physiological parameters of cardiac pacing, and
   instructions for resuming artificial pacing provided by the IMD.

5. The system of claim 4 further comprising an external device that provides instruction to the IMD for turning on or off the electronic pulse generator delivering artificial cardiac pacing halting and for obtaining data.

6. The system of claim 4 further comprising an external device that receives data on the one or more intrinsic physiological parameters of cardiac pacing and presents the data to a user.

7. The system of claim 1, wherein obtaining data on one or more intrinsic physiological parameters of cardiac pacing is initiated after a predefined interval after the halting of the artificial pacing provided by the implantable electronic pulse generator.

8. The system of claim 1, wherein the gene therapy comprises providing a hyperpolarization-activated cyclic nucleotide-gated (HCN) channel gene construct.

9. The system of any claim 1, wherein the intervention effecting cardiac pacing comprises cell therapy.

10. The system of claim 9, wherein the cell therapy comprises stem cell therapy or genetically modified cell therapy.

11. The system of claim 1, wherein the implantable electronic pulse generator comprises a pacemaker, ICD, CRT, CRT-D, SubQ ICD, intravascular pacemaker/ICD, and/or miniaturized leadless pacemaker.

12. The system of claim 1, wherein the instructions for recording and storing reference data for one or more intrinsic physiological parameters of cardiac pacing prior to the intervention effecting cardiac pacing, for halting the electronic pulse generator delivering artificial cardiac pacing at predetermined data collection intervals after the intervention effecting cardiac pacing, and/or instructions for obtaining data on one or more intrinsic physiological parameters of cardiac pacing during the predetermined data collection interval are executed on a processing circuit included within the implantable electronic pulse generator.

13. The system of claim 1, wherein the instructions for recording and storing reference data for one or more intrinsic physiological parameters of cardiac pacing prior to the intervention effecting cardiac pacing, for halting the electronic pulse generator delivering artificial cardiac pacing at predetermined data collection intervals after the intervention effecting cardiac pacing, and/or instructions for obtaining data on one or more intrinsic physiological parameters of cardiac pacing during the predetermined data collection interval are executed on a processing circuit included external to the implantable electronic pulse generator.

14. The system of claim 1 further comprising a means for storing the data on one or more intrinsic physiological parameters of cardiac pacing in memory of the implantable electronic pulse generator.

15. The system of claim 14 further comprising a means for the transmission of stored data to an external device.

16. The system of claim 15, wherein transmission of the stored data comprises uplink telemetry.

17. The system of claim 1 further comprising a means for presenting data on one or more intrinsic physiological parameters of cardiac pacing to a user.

18. The system of claim 1, wherein an intrinsic physiological parameter of cardiac pacing is indicative of the establishment of an exogenous biopacing intervention.

19. The system of claim 1, wherein an intrinsic physiological parameter of cardiac pacing further comprises an electrogram (EGM), pressure, or cardiac contractability.

20. The system of claim 1, wherein artificial pacing is halted for a period of about 30 seconds to about 180 seconds.

21. The system of claim 20, wherein data on one or more intrinsic physiological parameters of cardiac pacing is obtained after a predefined interval after halting artificial pacing.

22. The system of claim 1 comprising monitoring the response of the intervention effecting cardiac pacing to cardiac autonomic function.

23. A method of monitoring the functional effect of an intervention effecting cardiac pacing, the method comprising:
   recording and storing reference data for one or more intrinsic physiological parameters of cardiac pacing prior to the intervention effecting cardiac pacing;
   wherein the reference data recorded and stored for one or more intrinsic physiological parameters of cardiac pacing prior to the intervention effecting cardiac pacing a response to artificial cardiac pacing at the intervention site;
   wherein the intervention effecting cardiac pacing comprises gene therapy, cell therapy, ablation, and/or drug delivery;
   halting artificial pacing provided by an implantable electronic pulse generator to a heart subject to an intervention effecting cardiac pacing at predetermined data collection intervals after the intervention effecting cardiac pacing; and
   obtaining data on one or more intrinsic physiological parameters of cardiac pacing in the heart subject to an intervention effecting cardiac pacing during the predetermined data collection intervals.

24. A method of monitoring the functional effect of an intervention effecting cardiac pacing, the method comprising:
   recording and storing reference data for one or more intrinsic physiological parameters of cardiac pacing prior to the intervention effecting cardiac pacing;
   wherein the reference data recorded and stored for one or more intrinsic physiological parameters of cardiac pacing prior to the intervention effecting cardiac pacing comprises a response to artificial cardiac pacing at the intervention site;
   wherein the intervention effecting cardiac pacing comprises gene therapy, cell therapy, ablation, and/or drug delivery;
   providing one or more interventions that effect cardiac pacing;
   halting at predetermined data collection intervals after the intervention effecting cardiac pacing the artificial pacing provided by the implantable electronic pulse generator; and
   obtaining data on one or more intrinsic physiological parameters of cardiac pacing during the predetermined data collection intervals.

25. A computer program product in non- transitory, computer-readable recordable type medium, the computer program product comprising:
   instructions for recording and storing reference data for one or more intrinsic physiological parameters of cardiac pacing prior to the intervention effecting cardiac pacing;
   wherein the reference data recorded and stored for one or more intrinsic physiological parameters of cardiac pacing prior to the intervention effecting cardiac pacing comprises a response to artificial cardiac pacing at the intervention site;
   wherein the intervention effecting cardiac pacing comprises gene therapy, cell therapy, ablation, and/or drug delivery;
   instructions for an electronic pulse generator to deliver artificial cardiac pacing;
   instructions for halting the electronic pulse generator delivering artificial cardiac pacing at predetermined data collection intervals after the intervention effecting cardiac pacing; and
   instructions for obtaining data on one or more intrinsic physiological parameters of cardiac pacing during the predetermined data collection intervals.

26. The system of claim 1, further comprising an intrinsic physiological parameter of cardiac pacing selected from the group consisting of an injection site pacing electrogram, an intrinsic electrogram, an escape electrogram, and an ectopic beat electrogram.

27. The system of claim 1, wherein the system provides for displaying a stored intrinsic physiological parameter of cardiac pacing prior to the intervention effecting cardiac pacing in comparison to the data obtained on one or more intrinsic physiological parameters of cardiac pacing during the predetermined data collection interval.

28. The method of claim 23, further comprising an intrinsic physiological parameter of cardiac pacing selected from the group consisting of an injection site pacing electrogram, an intrinsic electrogram, an escape electrogram, and an ectopic beat electrogram.

29. The method of claim 23, further comprising displaying a stored intrinsic physiological parameter of cardiac pacing prior to the intervention effecting cardiac pacing in comparison to the data obtained on one or more intrinsic physiological parameters of cardiac pacing during the predetermined data collection interval.

30. The computer program product of claim 25, further comprising an intrinsic physiological parameter of cardiac pacing selected from the group consisting of an injection site pacing electrogram, an intrinsic electrogram, an escape electrogram, and an ectopic beat electrogram.

31. The computer program product of claim 25, wherein the computer program product provides for displaying a stored intrinsic physiological parameter of cardiac pacing prior to the intervention effecting cardiac pacing in comparison to the data obtained on one or more intrinsic physiological parameters of cardiac pacing during the predetermined data collection interval.

32. The method of claim 24, further comprising an intrinsic physiological parameter of cardiac pacing selected from the group consisting of an injection site pacing electrogram, an intrinsic electrogram, an escape electrogram, and an ectopic beat electrogram.

33. The method of claim 24, further comprising displaying a stored intrinsic physiological parameter of cardiac pacing prior to the intervention effecting cardiac pacing in comparison to the data obtained on one or more intrinsic physiological parameters of cardiac pacing during the predetermined data collection interval.

34. The system of claim 1, further comprising instructions for recording and storing event triggered data.

35. The system of claim 4, further comprising instructions for recording and storing event triggered data.

36. The methods system of claim 23, further comprising recording and storing event triggered data.

37. The method of claim 24, further comprising recording and storing event triggered data.

38. The computer program product of claim 25, further comprising instructions for recording and storing event triggered data.

39. The method of claim 23, wherein the gene therapy comprises providing a hyperpolarization-activated cyclic nucleotide-gated (HCN) channel gene construct.

* * * * *